United States Patent [19]
Sharma et al.

[11] Patent Number: 5,969,210
[45] Date of Patent: Oct. 19, 1999

[54] METHODS FOR THE CHARACTERIZATION OF COMPOUNDS WHICH STIMULATE STF-1 EXPRESSION IN PANCREATIC ISLET CELLS

[75] Inventors: Seema Sharma, La Jolla, Calif.; Marc R. Montminy, Wellesley, Mass.

[73] Assignee: Research Development Foundation, Carson City, Nev.

[21] Appl. No.: 08/786,527

[22] Filed: Jan. 21, 1997

Related U.S. Application Data

[60] Provisional application No. 60/010,414, Jan. 22, 1996.
[51] Int. Cl.$^6$ .............................. C12N 5/00; C12N 15/00; A61K 49/00
[52] U.S. Cl. ................................. 800/3; 800/14; 424/9.2; 435/30
[58] Field of Search ....................... 800/2, 3, 14; 435/29, 435/325, 354, 30; 424/9.2

*Primary Examiner*—Deborah Crouch
*Attorney, Agent, or Firm*—Benjamin Aaron Adler

[57] ABSTRACT

One embodiment of the present invention provides a method of testing for compounds which may induce STF-1 transcription. Pancreatic islet cells which express the STF-1/lacz fusion gene are isolated and the effect of various compounds on STF-1 expression is measured by adding the compound of interest to STF-1/lacZ expressing cells. LacZ activity in control and treated cells is then quantitated by a colorimetric assay. Using this method, a large number of compounds can be screened and STF-1 inducing compounds can be identified readily. Another embodiment of the present invention provides a method of using the STF-1 promoter to mark insulin producing pancreatic islet cells in vivo. In this regard, the green fluorescent protein (GFP) served as an indicator. The introduction of the STF-1 green fluorescent protein transgene into pigs allows for the efficient and rapid recovery of insulin producing cells from the pancreas.

9 Claims, 21 Drawing Sheets

| Interval | Recombinant / total | Recombination frequency (x100) ±SEM | 95% Confidence limits (lower-upper) |
| --- | --- | --- | --- |
| Nos1 | | | |
| Nos1-D5Hun12 | 14/92 | 15.22 ± 3.74 | 8.6-24.2 cM |
| D5Hun12-Zp3 | 0/92 | 0 | 0-3.9 cM |
| Zp3-Azgp | 1/94 | 1.06 ± 1.06 | 0-5.8 |
| Azgp-Pdx1 | 1/92 | 1.09 ± 1.08 | 0-5.9 |
| Pdx1-Pmv12 | 0/92 | 0 | 0-3.9 |
| Pmv12-Iapls3-9 | 0/93 | 0 | 0-3.9 |
| Iapls3-9-Actb | 6/93 | 6.45 ± 2.55 | 2.4-13.5 |

FIG. 1B

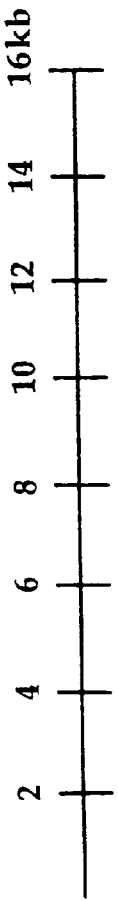

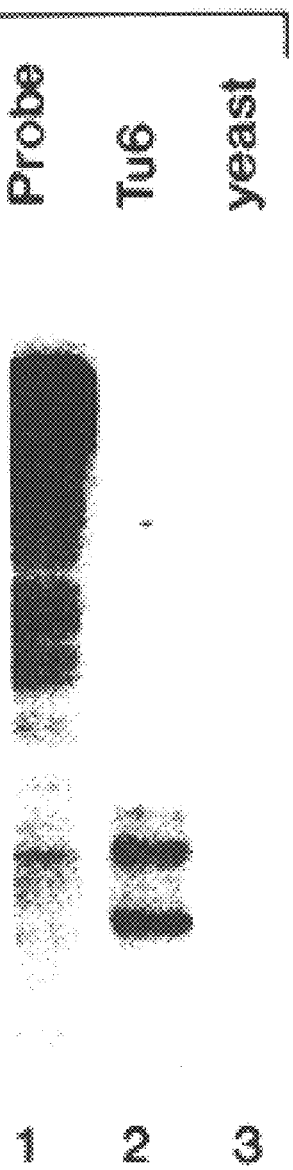
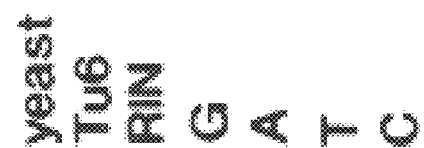
FIG. 2C
FIG. 2D

STF1 *lac z*
FIG. 3A
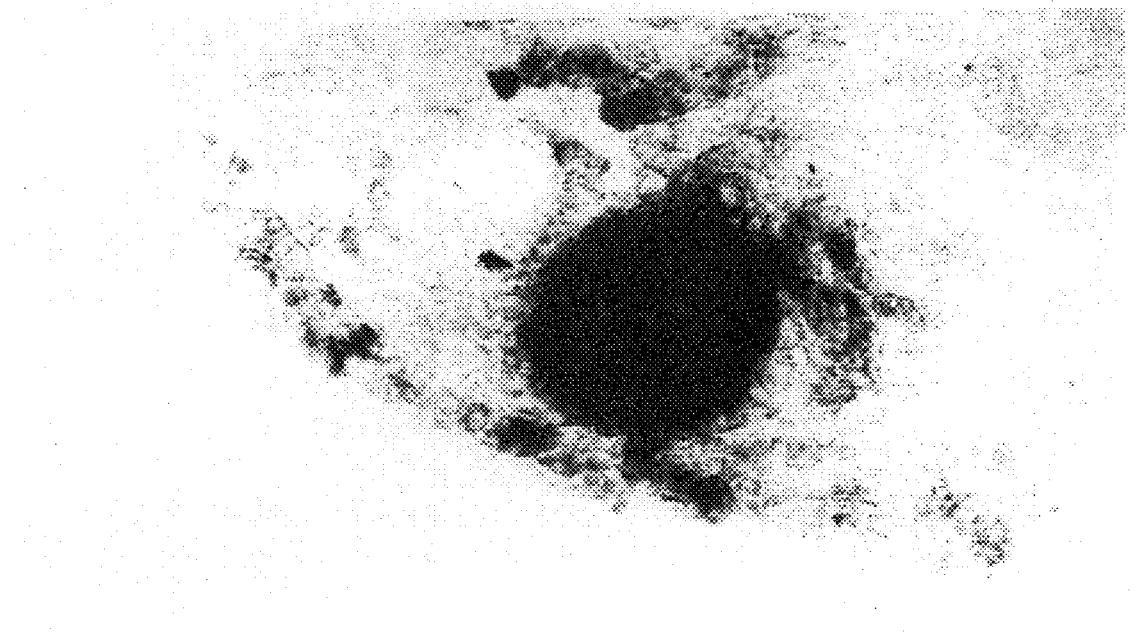
Control
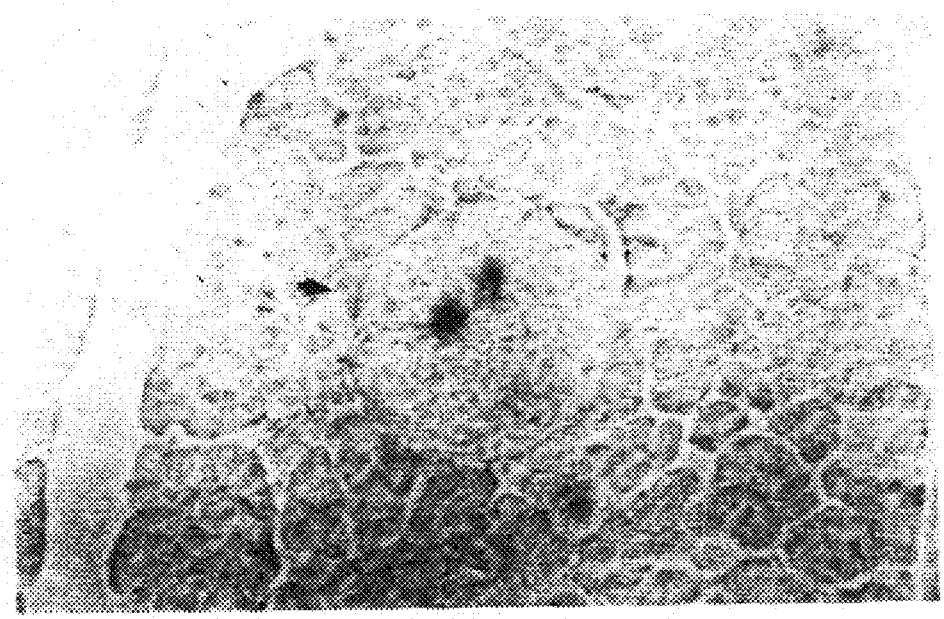
FIG. 3B

STF E Probe: E-WT E-MUT

C1-3
nonspecific→ free probe→

E-WT: CACGTG
E-MUT: AACGCG

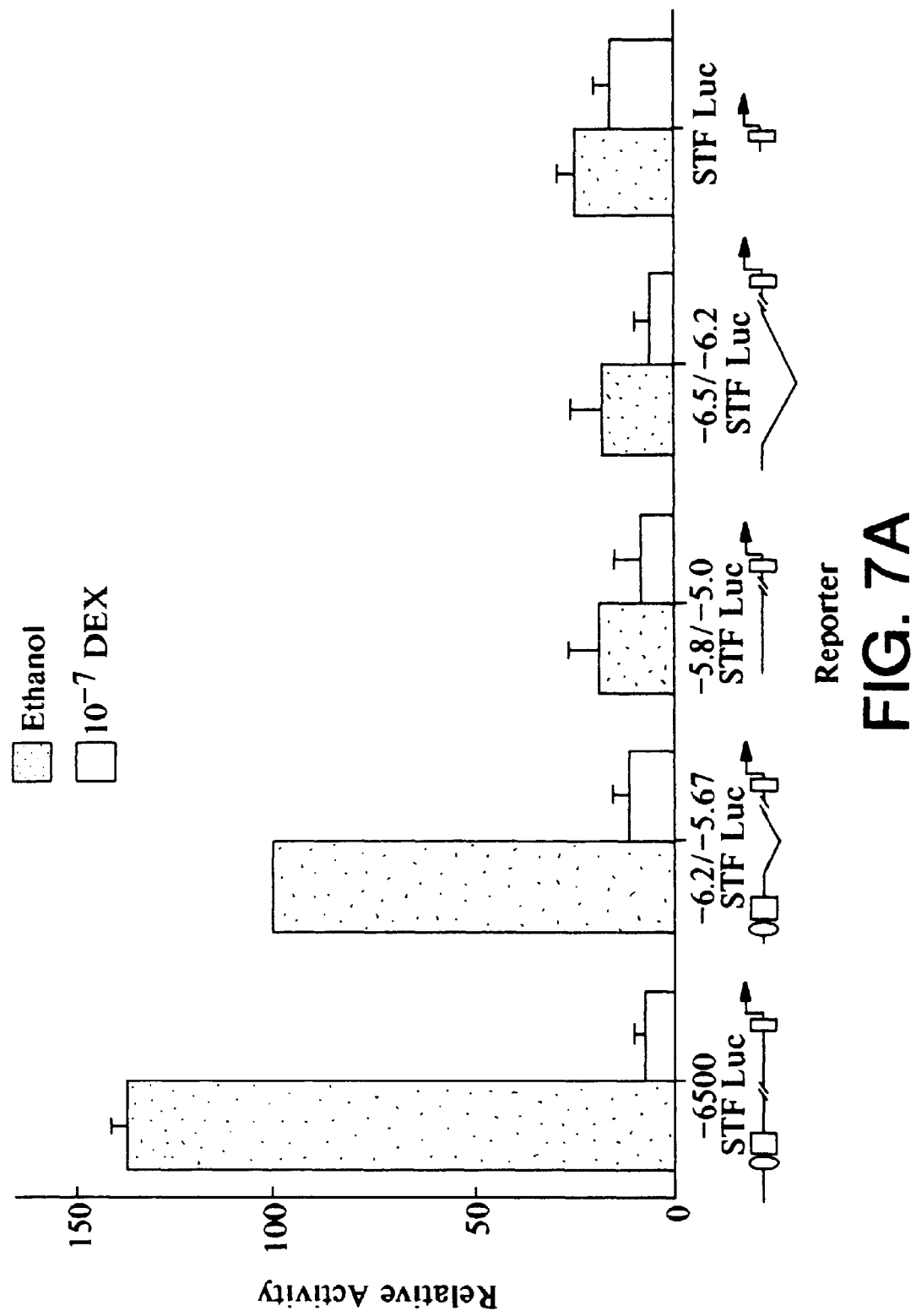

-6200

TCTAGAGAGTTCTCCTGTTCGCTAGATAAGAAAGCCTGTTCTGCCAT

CCCAGCAGGCATAGGCTGTTTAAGTTACTAGATAACAGAGTTGTTA

TTGATTCTATTATTATTATTTTTTCTACTCTTCCTGATTCCCTGAAGTC

CAAGGGAAGTTTTGTCAACTAGGAATGATTTTTGTTTAAAAAAAAA

E box

AAAAAAGGCTCCTTGTTGTGTCTTAGCTGGTCAGTGA<u>CAGATGG</u>A

GTCCTGAGTTTCCTAGGAGCCCTTTACTCAGGAGTGGGAGAACAGA

HNF-3 site

<u>AAGTAAATAAG</u>CGCTCTTAGTCATCTGCTTTCTCAGAGCAGCGTTG

GGCCCAGCACTTGGAAAGCGAATGCTGGCTCCTCCTGGACTCCCC

CGTCAGCCTGATGTTGTTAACCCGTTTAACATTCCCTTATCACATGC

TCATTGTGGGCAGAATTAAGTGGAATTAGCTAACAAATTATATAAA

ATTCATTTACCTTTCAAGGAAGCTG   (SEQ ID NO.: 2)

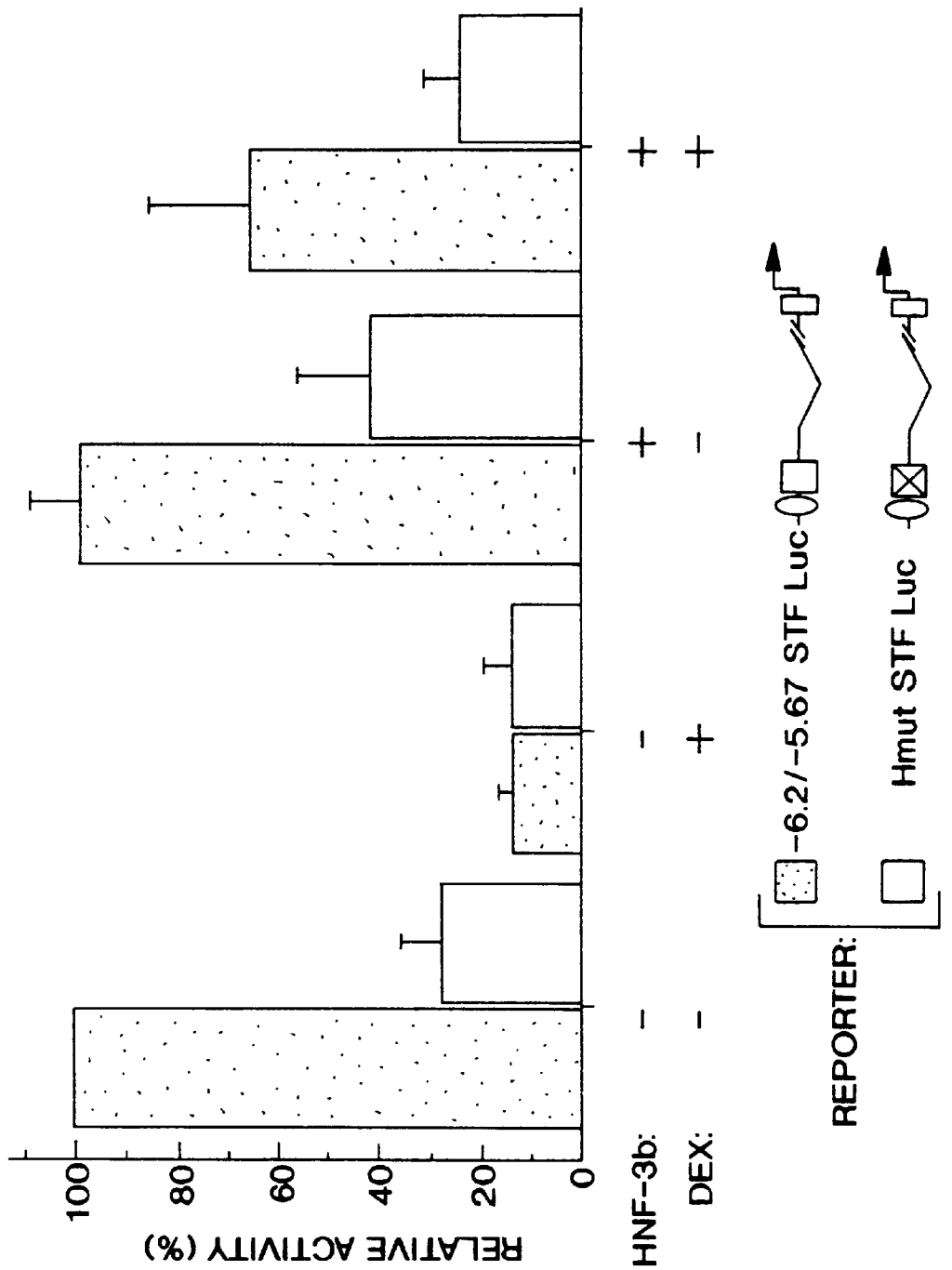

METHODS FOR THE CHARACTERIZATION OF COMPOUNDS WHICH STIMULATE STF-1 EXPRESSION IN PANCREATIC ISLET CELLS

This is application claims the benfit of U.S. Provisional Application Ser. No. 60/010,414, filed Jan. 22, 1996.

BACKGROUND OF THE INVENTION

1. Field of the Invention

The present invention relates generally to the fields of biochemical endocrinology, molecular biology and protein chemistry. More specifically, the present invention relates to novel methods for the characterization of compounds which stimulate STF-1 expression in pancreatic islet cells.

2. Description of the Related Art

Glucose homeostasis requires the concerted efforts of numerous neuroendocrine systems. The pancreatic islets are considered to be the primary "glucose sensor" in mammals. Pancreatic islets contain four populations of cells which are characterized primarily as insulin, glucagon, somatostatin or pancreatic polypeptide-producing cells. Among these, insulin-producing β-cells predominate. Insulin secretion and production are stimulated by increases in serum glucose, an event which i s mandatory for subsequent glucose uptake in certain tissues. Hence, dysfunction or destruction of β-cells results in elevated serum glucose levels, ultimately developing into diabetes mellitus.

Genetic linkage analysis indicates that hereditary factors strongly influence susceptibility to acquisition of the diabetic state. For example, at least 18 genetic loci have some degree of linkage to insulin-dependent diabetes mellitus (IDDM). One disease susceptibility locus, termed IDDM2, encompasses the human insulin gene and is associated with altered transcriptional regulation of insulin promoter function. Hence, disruption of the processes that regulate insulin gene expression may account in part for diabetogenesis. Consistent with this hypothesis, impaired β-cell function is a very common feature of diabetes.

Non-insulin dependent diabetes mellitus (NIDDM) i s thought to occur as a result of both external and complex genetic influences. Interestingly, allelic variants at the insulin locus itself have been associated with the disease. These variants appear to contain a normal insulin gene, but exhibit altered properties with regard to transcriptional regulation.

Estimates indicate that as many as 20 million Americans may suffer from non-insulin dependent diabetes mellitus (Type II) diabetes. The progression of the disease appears to require both environmental factors and certain as yet largely unidentified diabetes susceptibility genes, which may contribute to the peripheral insulin resistance of Type II diabetes, in which tissues fail to utilize glucose appropriately in response to the insulin signal. Alternatively, genetic factors may account for the reduced glucose sensitivity of the insulin-producing pancreatic β-cells in these individuals. The end result of both of these physiological states is the marked hyperglycemia which constitutes the primary hallmark of diabetes.

Transcriptional control of the insulin gene is achieved through a short region of flanking DNA that interacts with cell-specific and glucose-sensitive signaling molecules. The precise nature of this regulatory organization remains poorly understood, although it is generally acknowledged that basic helix-loop-helix (bHLH) and homeodomain-containing factors are critical components of the transcriptional machinery that governs β-cell-specific expression of insulin. An islet-specific basic helix-loop-helix complex interacts with a proximal E-box that has been variously termed Nir, IEBl or ICE; this element is present twice in the rat insulin I gene, but only once in the rat insulin II and human insulin genes.

Transient assays in insulin-producing cell lines suggest that E-box-binding factors synergize with β-cell-specific proteins that bind a nearby AT-rich sequence termed FLAT, which bears the hallmarks of a homeodomain recognition sequence. Several characterized homeodomain proteins have been shown to bind the FLAT element, including Isl-1, 1mx-1, cdx-3 and STF-1. In addition, the latter of these corresponds to the principal binding activity at a n evolutionarily conserved AT-rich sequence termed the P-element. Isl-1 binds the FLAT element weakly and does not appear to be present in the FLAT-binding complexes detected with extracts from insulin-producing cells. Current evidence supports a more important role for Isl-1 in neural development. The homeodomain factors 1mx-1 and cdx-3 have interesting transactivation properties with regard to insulin promoter function in heterologous cells, but their cellular distribution and FLAT-binding ability inside the β-cell remains unclear. In addition, there is little data that directly address the function of these factors in β-cell lines.

Within the group of factors with insulin promoter-binding activity, STF-1 is perhaps the most promising candidate for a bona fide regulator of insulin promoter function. In mice, STF-1 is first detected at embryonic day 8.5 in the nuclei of primordial cells that gives rise to the pancreas, shortly prior to the earliest detected expression of insulin in this region. Throughout the ensuing development of the endocrine pancreas, STF-1 and insulin are largely co-expressed. In addition, in extracts from insulin-producing cells lines, STF-1 appears to be a component of the endogenous DNA-binding activity at both the FLAT and P elements in the insulin promoter. STF-1 also strongly synergizes with the E-box-binding factor Pan-1, as might be expected from a FLAT-binding factor. However, DNA-binding assays indicate that other, unknown, factors from β-cell extracts also make a large contribution to the detected FLAT-binding activity. It remains unclear whether FLAT-mediated insulin promoting activity requires all, or only a subset, of these detected species.

Although STF-1 is initially expressed in both exocrine and endocrine cells of the developing pancreas, the production of STF-1 is progressively restricted to insulin- and somatostatin-producing islet cells. In these cells, STF-1 action appears to be important for maintaining high level expression of both somatostatin and insulin genes.

STF-1 recognizes two well defined islet-specific elements on the insulin promoter, termed FLAT and P. When bound to these sites, STF-1 stimulates insulin transcription in concert with E47, a helix-loop-helix protein which recognizes two E-box elements termed Far and Nir. Similarly, STF-1 regulates somatostatin expression in islet cells via two islet specific elements, termed TSEI and TSEII.

Homeodomain proteins such as STF-1 have been found to play an important role in development by establishing cell or segmental identity. In contrast to their specific and distinct effects in vivo, most homeodomain proteins exhibit low and overlapping DNA binding specificity in vitro. However, recent studies have implicated certain protein co-factors as determinants of homeodomain DNA binding specificity in vivo. In Drosophila, for example, extradenticle (exd) has been shown to modulate the activity of homeotic proteins without altering their pattern of expression. Rather, extradenticle appears to promote target gene selection by enhancing the DNA binding specificity of certain homeodomain proteins. Indeed, extradenticle is highly conserved in vertebrates, sharing extensive sequence similarity (71%) with the human protooncogene Pbx1.

The commitment of cells to specific lineages during development is determined in large part by the relative expression of various homeodomain (HOX) selector proteins which mediate the activation of distinct genetic programs. But the mechanisms by which individual HOX genes are themselves targeted for expression in different cell types remains largely uncharacterized.

The vertebrate pancreas consists of endocrine and exocrine components which arise from a common progenitor cell in the duodenal anlage (1). Within the endocrine component of the pancreas, a pluripotent precursor cell which initially expresses multiple islet hormones undergoes progressive restriction to form the four subpopulations of cells comprising the adult islets of Langerhans: insulin, somatostatin, glucagon, and pancreatic polypeptide-producing cells (2, 3). The mechanism by which these developmental pathways are activated is unclear, but current evidence implicates the homeobox factor STF-1 (IPF-1/IDX-1) as an important determinant in this process. Indeed, the requirement for STF-1 in development is supported by homologous recombination studies in which targeted disruption of the STF-1/IPF-1 gene leads to congenital absence of the pancreas (4).

STF-1 (also referred to as Pdx1) expression is first detectable at embryonic day 8.5 in cells of the pancreatic anlage and in pluripotent precursor cells. Transiently expressed in both endocrine and exocrine components of the developing pancreas, STF1 production is progressively restricted to insulin and somatostatin producing islet cells (5, 6). In these cells, STF-1 appears to regulate both insulin and somatostatin genes by binding to functional elements within each promoter (5, 7–16).

The prior art is deficient in the lack of effective means of regulating expression of the homeodomain protein STF-1 in pancreatic cells. The present invention fulfills this long-standing need and desire in the art.

SUMMARY OF THE INVENTION

Although STF-1 is an important regulator of pancreatic genes, the mechanism by which STF-1 expression is itself targeted to pancreatic cells remains uncharacterized. The present invention demonstrates that a 6.5 kb fragment of the STF-1 promoter is sufficient to direct islet specific expression of a β-galactosidase reporter gene in transgenic mice as well as in cultured duodenal cells. Within this 6.5 kb fragment, an E box element, located at −104 relative to the major transcription initiation site is particularly critical for STF-1 promoter activity. This element is recognized by an upstream activator which is essential for islet expression of STF-1. Indeed, this STF-1 promoter is 20–100 fold more active in enhancing targeted expression of STF-1 in islet cells. Deletion of the proximal E box sequence at −104 completely abolished STF-1 expression in HIT cells. Furthermore, anti-USF (upstream factor) antiserum inhibited the formation of C1, C2 and C3 indicating that these proteins are formed by the USF protein.

Further, an STF-1 enhancer element has been found in a 530 bp region which extends 600 bp upstream of the transcriptional initiation site. Promoter constructs containing this 530 bp fragment were repressed fully by dexamethosone treatment but a minimal STF-1 promoter construct containing the ubiquitous USF-1 recognition site was not. The 530 bp region was 5–10 fold more active in HIT-T15 cells compared to COS-7 cells, demonstrating that this fragment contains islet cell specific activity. Thus, the STF-1-lacZ fusion gene is used in the present invention to screen for compounds which enhance STF-1 expression in pancreatic islet cells. Compounds which stimulate STF-1 production enhance pancreatic islet B cell function, i.e., production of insulin. Thus, compounds identified by the method described by the present invention are particularly useful in patients with Type II diabetes mellitus in which there is an intolerance to glucose due to borderline islet cell function.

In one embodiment of the present invention, there is provided a method of testing for compounds which induce STF-1 transcription.

Pancreatic islet cell lines which express the STF-1/lacz fusion gene are isolated using calcium phosphate co-precipitation. To examine the effect of various compounds on STF-1 expression, the compound of interest is added to STF-1/lacZ expressing cells. LacZ activity in control and treated cells is then quantitated by a colorimetric assay. Using this method, a large number of compounds can be screened and STF-1 inducing compounds can be identified readily.

In one embodiment of the present invention, there is provided a method of using the STF-1 promoter to mark insulin producing pancreatic islet cells in vivo. In this regard, the green fluorescent protein (GFP) served as an indicator. The expression of the green fluorescent protein can be detected without disrupting as described in Ogawa et al. *Proc. Natl. Acad. Sci.*, 1995, 92:11899–11903. To facilitate the recovery of β cells from an animal's pancreas, the STF-1 promoter was fused to the gene encoding the GFP. The introduction of the STF-1-green fluorescent protein transgene into pigs allows for the efficient and rapid recovery of insulin producing cells from the pancreas. Briefly, the pancreas is recovered from pigs and treated with collagenase to disperse the cells. Insulin producing islet cells are efficiently recovered b y fluorescence activated cell sorting (FACS) based on the expression of the STF-1 green fluorescent protein transgene. The purified population of β cells can be used in cellular therapy of diabetic patients.

In one aspect of the present invention, there is provided a method for determining an ability of a test compound to stimulate pancreatic islet cells to induce STF-1 transcription, comprising the steps of: providing a vector containing an STF-1 enhancer having a sequence selected from the group SEQ ID No:1 or SEQ ID No:2 or fragments thereof, a promoter, and a reporter gene under the transcriptional control of both said STF-1 enhancer and said promoter, wherein said reporter gene is capable of conferring a detectable signal to said host cell; transferring said vector into said host cell; culturing said host cell in the presence of a test compound to determine an ability of said test substance to stimulate said host cell to produce said signal; and assaying for said signal to determine said ability of said test compound to stimulate said host cell to produce said detectable signal, wherein a presence of said signal indicates that said test compound stimulates pancreatic islet cells to induce STF-1 transcription, and wherein an absence of said signal indicates that said test compound does not stimulate pancreatic islet cells to induce STF-1 transcription.

In a preferred embodiment of this object of the present invention, the reporter gene used is an enzyme. In a more preferred embodiment, the enzyme is selected from the group of luciferase and β-galactosidase.

In another embodiment of the present invention, said transferring step is performed by transfection or by microinjection introduction of a transgene into animals.

In another object of the present invention, there is provided a method for marking insulin-producing pancreatic islet cells in vivo, comprising the steps of: providing a vector containing an STF-1 promoter and a reporter gene under the transcriptional control of said STF-1 promoter, wherein said reporter gene is capable of conferring a detectable signal to a pancreatic islet cell; introducing said vector as a transgene into an animal embryo; growing said embryo to an animal with pancreatic islet cells; and assaying for said detectable signal to determine if any of said animal's pancreatic islet cells express said reporter gene, wherein a presence of signal indicates a presence of insulin-producing pancreatic islet cells, and wherein an absence of signal indicates an absence of insulin-producing pancreatic islet cells.

In a preferred embodiment of this object of the present invention, the reporter gene produces a fluorescent protein, and the method further includes a step of sorting insulin-producing pancreatic islet cells from non-insulin-producing pancreatic islet cells by fluorescence activated cell sorting (FACS).

Other and further aspects, features, and advantages of the present invention will be apparent from the following description of the presently preferred embodiments of the invention.

BRIEF DESCRIPTION OF THE DRAWINGS

So that the matter in which the above-recited features, advantages and objects of the invention are attained and can be understood in detail, more particular descriptions of the invention summarized briefly above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1(A–B) shows the chromosomal location of the STF-1 gene. FIG. 1B is a table showing the recombination frequency between STF-1 and various markers on chromosome 5. The left column indicates markers employed for chromosomal assignment. STF-1 is referred to here as Pdx1.

FIGS. 2(A–D) shows the STF-1 promoter is TATA-less and utilizes multiple transcription initiation sites. FIG. 2A shows a schematic representation of the 15 kilobase genomic clone of STF-1 with the kilobase scale above. The 6.5 kilobase 5' flank, the 4 kilobase intron, and the 3 kilobase 3' flank are indicated. IVS refers to the 4 kilobase intron which interrupts exons I (shaded and indicated as I) and II (shaded and indicated as II). FIG. 2B shows the nucleotide sequence of the 5' flanking region of the STF-1 gene (SEQ ID NO:1). Transcription start sites mapped by RNase protection (filled arrowheads) and primer extension (empty arrowheads) are indicated as S1 (the major initiation site, bold), S2, and S3. Potential upstream factor binding sites for bHLH/bHLH-ZIP proteins (E box), CTF/NF-1 (CAAT) and C/EBP are underlined and labeled along with their locations relative to the major start site. FIG. 2C shows an RNase protection assay of Tu6 RNA (Tu6, lane 2) or control yeast tRNA (yeast, lane 3) using anti-sense STF-1 RNA probe. Undigested probe is shown on left (lane 1). FIG. 2D, shows the results of primer extension analysis on yeast (lane 4), Tu6 mRNA (lane 5) or RIN mRNA (lane 6) using an anti-sense STF-1 primer. A sequencing ladder is shown on the far right (GATC, lanes 7–10). Correspondence between RNase protected products and primer extended products are marked and the first three start sites designated S1, S2, and S3 are shown (see also FIG. 2B, bottom).

FIGS. 3(A–B) shows a 6.5 kb fragment of the STF-1 promoter targets expression of a β-galactosidase reporter gene to pancreatic islet cells of transgenic mice. Representative cryosections of adult pancreas from transgenic FIG. 3A and control FIG. 3B littermates were evaluated for lacZ activity using Xgal as chromogenic substrate. Arrows point to the pancreatic islet cells.

FIGS. 4(A–B) shows that the distal and proximal elements within the STF-1 promoter direct STF-1 expression to pancreatic islet cells.

FIGS. 5(A–D) shows that a proximal E-box element in the STF-1 promoter binds the upstream factor USF.

FIGS. 6(A–B) illustrates that the binding of USF to the –104 E-box is important for STF-1 promoter activity.

FIGS. 7(A–B) demonstrates that glucocorticoids repress STF-1 expression via an islet specific enhancer in the 5' flanking region of the STF-1 gene.

FIG. 7A: Shown is the activity of STF-1 promoter constructs following treatment of HIT-T15 cells with dexamethasone ($10^{-7}$M) or control ethanol vehicle for 18–24 hours. The activity of −6.2/−5.67 STF Luc reporter is set at 100%. All constructs were evaluated in the context of a STF-1 luciferase vector (STF-1 Luc) which contains 120 bases of 5' proximal flanking region. The STF-1 sequences inserted into the STF-1 Luc reporter are indicated by nucleotide numbers. For example, −6.5/−6.2 STF Luc contains STF-1 sequences from −6500 to −6200 fused to the proximal 120 bases of STF-1 5' flanking region. Distal regions which contain activating elements are indicated by an oval and square, and the minimal STF-1 promoter is indicated by rectangle. Standard error bars are shown. Assays were repeated at least three times. STF-1 reporter activity throughout was normalized to transfection efficiency using a co-transfected CMV-pgal control plasmid.

FIG. 7C. The nucleotide sequence of the minimal islet specific enhancer in the STF-1 gene which extends from −6.2 to −5.67 kb is shown (SEQ ID NO:2). HNF-3 and E box binding motifs are bolded and underlined.

FIGS. 8(A–B) demonstrates that the pancreatic islet specific enhancer in the STF-1 gene contains binding sites for HNF-3β and BETA-2.

FIG. 9 demonstrates that glucocorticoids inhibit STF-1 expression by blocking HNF-3 activity on the islet specific enhancer.

FIG. 9B demonstrates the effect of HNF-3β overexpression on wild type (dark bars) and H-element mutant (light bars) STF-1 reporter activity in control (−) and dexamethasone (+) treated HIT-T15 cells. The activity of wild-type −6.2/−5.7 STF Luc construct containing minimal islet specific enhancer(−6200 to −5700) in control cells set at 100%. Standard error bars shown. Experiments were repeated at least four times.

DETAILED DESCRIPTION OF THE INVENTION

Figure 1A:
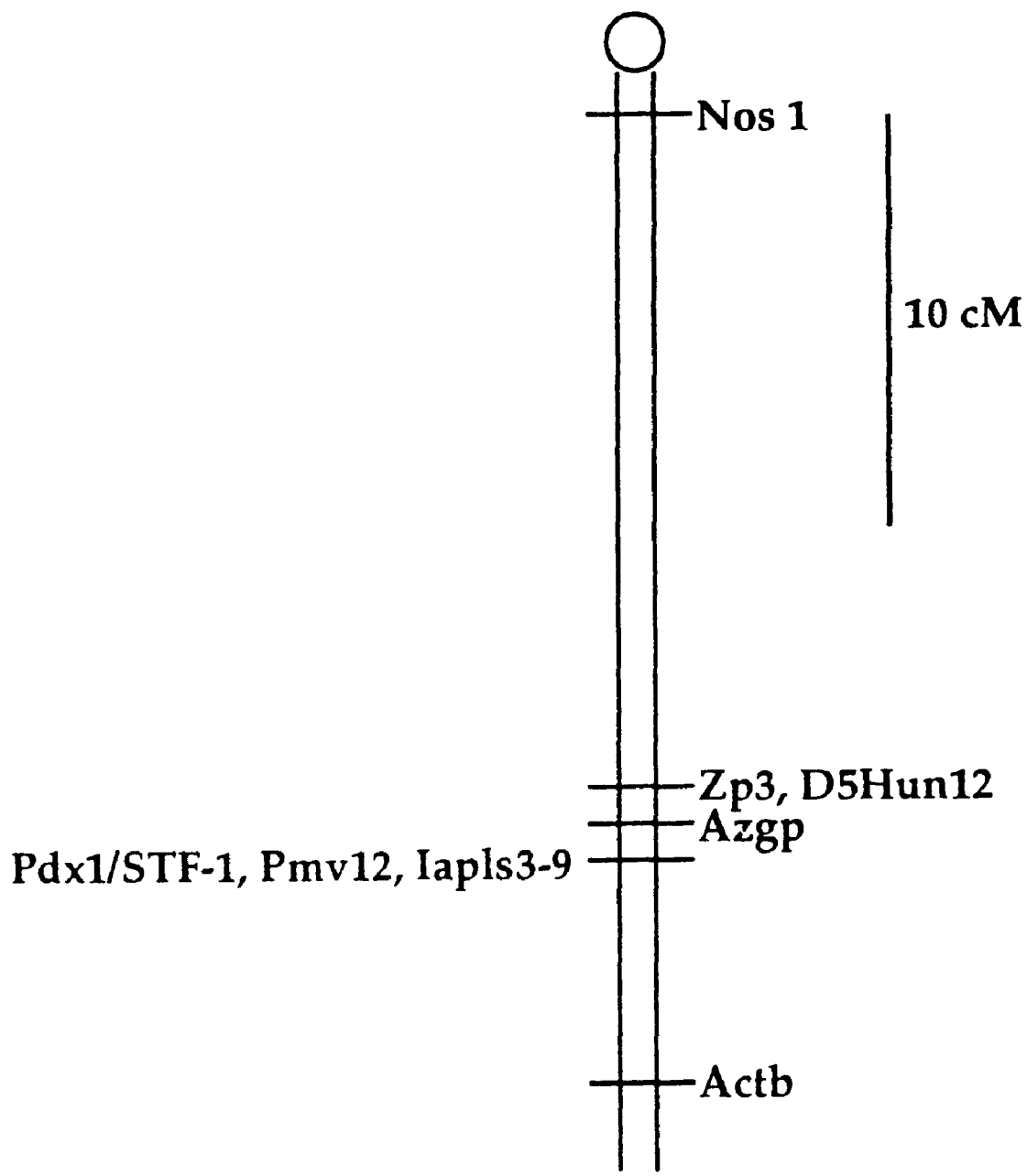
FIG. 1A shows that the STF-1 gene is encoded by an orphan homeobox gene located in the distal region of chromosome 5 (mouse) in a schematic diagram showing the position of STF-1 (referred to as Pdx1) relative to other markers on mouse chromosome 5. A centimorgan scale is indicated on right.

In the present invention, it was demonstrated that STF-1, a homeodomain protein which functions in pancreatic morphogenesis and in glucose homeostasis, is encoded by an "orphan" homeobox gene on mouse chromosome 5. When fused to a β-galactosidase reporter gene, a 6.5 kilobase genomic fragment of 5' flanking sequence from the STF-1 gene shows pancreatic-islet specific activity in transgenic mice. Two distinct elements within the STF-1 promoter are required for islet restricted expression—a distal enhancer sequence located between −3 and −6.5 kilobases and a proximal E box sequence located at −104, which is recognized primarily by the helix loop helix (bHLH)/leucine zipper (ZIP) nuclear factor USF. As point mutations within the −104 E box which disrupt USF binding correspondingly impair STF-1 promoter activity, the present invention demonstrates that USF is an important component of the regulatory apparatus which directs STF-1 expression to pancreatic islet cells. Further, it was found that glucocorticoids potently repressed the expression of the STF-1 gene by blocking the activity of a distal islet specific enhancer which recognizes two endodermal factors: HNF-3β and BETA-2/E47. Mutations in the STF-1 enhancer which blocked binding of either HNF-3β or BETA-2/E47 correspondingly disrupted STF-1 promoter activity. The ability of an HNF-3β expression vector to rescue STF-1 enhancer activity in glucocorticoid treated cells reveals that HNF-3β is indeed a n important regulator of STF-1 expression One object of the present invention is to provide a method for testing for compounds which induce STF-1 transcription. Pancreatic islet cell lines which express the STF-1/lacz fusion gene are isolated using calcium phosphate co-precipitation. To examine the effect of various compounds on STF-1 expression, the compound of interest is added to STF-1/lacZ expressing cells. LacZ activity in control and treated cells is quantitated by a colorimetric assay. Using this method, a large number of compounds can be screened and STF-1 inducing compounds can be identified readily.

In another object of the present invention, there is provided a method of using the STF-1 promoter to mark insulin-producing pancreatic islet cells in vivo. In this regard, the green fluorescent protein (GFP) has served as a vital indicator. The expression of the GFP can be detected without disrupting the cells as described in Ogawa et al. Proc. Natl. Acad. Sci., 1995, 92:11899–11903. To facilitate the recovery of β cells from an animal's pancreas, the STF-1 promoter has been fused to the gene encoding the GFP. The introduction of the STF-1- GFP transgene into pigs allows for the efficient and rapid recovery of insulin producing cells from the pancreas. Briefly, the pancreas is recovered from pigs and treated with collagenase to disperse the cells. Insulin producing islet cells are recovered by fluorescence activated cell sorting (FACS) based on the expression of the STF-1 green fluorescent protein transgene. The purified population of β cells is then be used in cellular therapy of diabetic patients.

In one aspect of the present invention, there is provided a method for determining an ability of a test compound to stimulate pancreatic islet cells to induce STF-1 transcription, comprising the steps of: providing a vector containing an STF-1 enhancer having a sequence selected from the group SEQ ID No:1 or SEQ ID No:2 or fragments thereof, a promoter, and a reporter gene under the transcriptional control of both said STF-1 enhancer and said promoter, wherein said reporter gene is capable of conferring a detectable signal to said host cell; transferring said vector into said host cell; culturing said host cell in the presence of a test compound to determine a n ability of said test substance to stimulate said host cell to produce said signal; and assaying for said signal to determine said ability of said test compound to stimulate said host cell to produce said detectable signal, wherein a presence of said signal indicates that said test compound stimulates pancreatic islet cells to induce STF-1 transcription, and wherein an absence of said signal indicates that said test compound does not stimulate pancreatic islet cells to induce STF-1 transcription.

In a preferred embodiment of this object of the present invention, the reporter gene used is an enzyme. In a more preferred embodiment, the enzyme is selected from the group of luciferase and β-galactosidase.

In another embodiment of the present invention, said transferring step is performed by transfection or by microinjection introduction of a transgene into animals.

In another object of the present invention, there is provided a method for marking insulin-producing pancreatic islet cells in vivo, comprising the steps of: providing a vector containing an STF-1 promoter and a reporter gene under the transcriptional control of said STF-1 promoter, wherein said reporter gene is capable of conferring a detectable signal to a pancreatic islet cell; introducing said vector as a transgene into an animal embryo; growing said embryo to an animal with pancreatic islet cells; and assaying for said detectable signal to determine if any of said animal's pancreatic islet cells express said reporter gene, wherein a presence of signal indicates a presence of insulin-producing pancreatic islet cells, and wherein an absence of signal indicates an absence of insulin-producing pancreatic islet cells.

In a preferred embodiment of this object of the present invention, the reporter gene produces a fluorescent protein, and the method further includes a step of sorting insulin-producing pancreatic islet cells from non-insulin-producing pancreatic islet cells by fluorescence activated cell sorting (FACS).

The human genome contains four clusters of genes, termed Hox or homeotic selector genes, which are critical determinants of axial body pattern formation during embryogenesis (Krumlauf, 1994 Cell 78:191–201). The four clusters each contain up to 13 genes, and a given gene in one cluster usually has particularly high homology with a member of the other three families. Such related genes are termed paralogs; hence HoxA1, HoxB1, HoxC1 and HoxD1 are all closely related paralogs, each in a different Hox cluster on a different chromosome. The HoxB complex is on the long arm of chromosome 17, and for example, HoxB1 through HoxB9 had been identified.

Glucose-dependent regulation of the insulin gene appears to occur in concert with glucose-mediated increases in the secretion of insulin. This may be due in part to increases in intracellular calcium. In addition, glucose-responsive insulin promoter function may occur at least in part by modulating the activity of FLAT-binding proteins. HoxB13 binds the functionally important FLAT lement of the insulin promoter with high affinity. Additionally, HoxB13 and the insulin ICE/Nir element-binding factor Pan-1 strongly activate the insulin promoter when added in combination. This is consistent with the observation that the FLAT and Nir elements function synergistically in insulin-producing cells. Collectively, these data suggested that calcium-dependent signaling pathways might regulate the function of HoxB13.

In accordance with the present invention there may b e employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease SI), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than eight. Its exact size will depend upon many factors which, in turn, depend upon the ultimate function and use of the oligonucleotide.

The term "primer" as used herein refers to a n oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or eterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or a common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used i n these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The following examples are given for the purpose of illustrating various embodiments of the invention and are not meant to limit the present invention in any fashion.

EXAMPLE 1

Chromosome Mapping

Chromosome mapping of the STF-1 gene was performed using a (B6xSPRET)F1xSPRET backcross panel of DNAs from The Jackson Laboratory Backcross DNA Panel Map Service using a $^{32}$P-labeled STF-1 cDNA fragment as a probe.

EXAMPLE 2

Generation of transgenic mice and β galatosidase staining

A fusion gene containing 6500 base pairs of upstream F-1 sequence in front of the β-galatosidase reporter gene was nstructed using standard cloning techniques and injected into male nuclei of fertilized oocytes. Founder mice were identified using thern blotting and PCR amplification techniques. Expression of STF-1/β-galatosidase gene in transgenic tissues was evaluated on 20 μM sections of paraformaldehyde fixed tissues using X-gal as omogenic substrate.

EXAMPLE 3

Antibodies

Nondiscriminating USF-1,2 antibodies used in supershift experiments were purchased from Santa Cruz Biotechnology. TFE3 antibodies were obtained from K. Jones. Antibodies which specifically recognize USF-1 or USF-2 were provided by M. Sawadogo (17, 18).

EXAMPLE 4

Isolation of STF-1 genomic clones

The STF-1 gene was isolated from an EMBL 3 rat genomic library using a $^{32}$P-labeled STF-1 cDNA fragment as a hybridization probe. STF-1 positive genomic fragments were subcloned into the EcoRI sites of the SK II plasmid (Stratagene).

EXAMPLE 5

RNase Protection and Primer Extension

Poly A$^+$ RNA was prepared using an Oligotex(dT)30 system (Quiagen). Oligonucleotide primers for primer extension analysis were 5' end labeled using γ$^{32}$P ATP and T4 polynucleotide kinase. 5 μg PolyA$^+$ RNA was incubated with end-labeled antisense primer at 80° C. for 5 minutes followed by 16 hours incubation at 42° C. Primer extension reactions were performed using AMV reverse transcriptase at 37° C. for 1 hour and the products were analyzed on 5% denaturing polyacrylamide. RNase protection analysis was performed using 25 μg of total RNA extracted from Tu6 cells (19). An antisense STF-1 RNA probe was generated using a STF-1 genomic fragment extending from –185 to +93 relative to the translation start site. $^{32}$P-labeled antisense STF-1 RNA was synthesized in vitro using T7 RNA Polymerase and $^{32}$P-UTP. STF-1 antisense RNA probe and mRNAs were annealed at 80° C. for 5 minutes followed by 16 hours of incubation at 65° C. Annealing reactions were subsequently treated with 40 μg/ml RNase at room temperature, 1 hour, and the digestion products were analyzed on 5% denaturing polyacrylamide electrophoresis.

EXAMPLE 6

Reporter clones and transient transfections

All promoter fragments were cloned into the p(A)3 luciferase backbone, provided by D. Helinski (20) using standard cloning methods. 5' flanking sequences from the STF-1 promoter were fused to the luciferase gene at +68 (–6500 STF Luc, –3500 STF Luc, –540 STF Luc, –410 STF Luc, –225 STF Luc, –140 STF Luc) or at +78 (–190 STF Luc, –130 STF Luc, –120 STF Luc, –95 STF Luc, –35 STF Luc) relative to the major transcriptional initiation site. Plasmids were transfected into HIT-T15 cells (ATCC), βTC 3 (provided by D. Hanahan (21)), PC12, COS, and HeLa cells by calcium phosphate precipitation. Luciferase values were quantitated on a Monolight luminometer and normalized to CAT activity derived from a cotransfected RSV-CAT internal control plasmid.

EXAMPLE 7

Gel shift assays and DNase Protection Assays

For electrophoretic mobility shift assays, oligonucleotide probes were labeled with α$^{32}$P-dCTP by fill-in reaction using Klenow fragment. 4 μg of nuclear extract was incubated with 0.5 ng of $^{32}$P-labeled, double stranded oligonucleotide and subjected to nondenaturing polyacrylamide electrophoresis as described previously (9). For supershift analysis, proteins were preincubated with the antibody followed by incubation with radioactive double stranded oligonucleotide and electrophoresis. DNase protection assays were performed as previously described (22).

Figures for DNA binding assays were scanned from original photos using an HP ScanJet 3C and assembled with Canvas software on a Macintosh. Scanned images were reproduced on a Tektronix Phaser II SDX.

EXAMPLE 8

Chromosomal location and genomic organization of the STF-1 gene

Using the STF-1 cDNA as hybridization probe on a backcross panel of DNAs from Jackson Laboratories, the single copy STF-1 gene was mapped to the distal region of mouse chromosome 5 (FIG. 1A). No recombinants were found with the distal markers Pmv12 or Iapls3–9 while six recombinants were observed with the more distal Actb locus (FIG. 1B). These results predict that the STF-1 gene would correspondingly be found on rat chromosome 14 and human chromosome 7q, loci which do not correspond to any of the four homeotic HOX clusters. These results indicate that STF-1 should be classified as an "orphan" homeobox gene.

To isolate the gene encoding STF-1, 106 bacteriophage clones were screened from a rat EMBL 3 genomic library with a $^{32}$P-labeled STF-1 cDNA probe and obtained two positive clones, each containing a genomic insert of 15 kilobases (kilobases). In addition to 6.5 kilobases of 5' flanking and 3.5 kilobases of 3' flanking sequence, the 15 kilobases STF-1 genomic fragment contained the entire STF-1 coding region which was interrupted by a single 4 kilobase intron inserted immediately upstream (Ala 135) of the homeobox coding sequence (amino acid 140-215) (FIG. 2A).

A consensus TATA box and initiator sequences in the 5' flanking region of the STF-1 genomic clone (FIG. 2B) were absent. Next, the transcriptional initiation sites for this gene were mapped. Using RNase protection and primer extension analysis on mRNAs from the insulin producing cell lines RIN and Tu6 (FIG. 2C and FIG. 2D), three principle initiation sites, termed S1, S2, and S3, were identified which were located 91, 107, and 120/125 nucleotides upstream of translational start site, respectively. A fourth minor transcriptional initiation site 137 nucleotides upstream of the translational start site was also observed. Like other TATA-less promoters, the STF-1 promoter contains G/A and G/C rich sequences 30 base pairs upstream of the S1 and S2 start sites (23–25).

EXAMPLE 9
STF-1 promoter activity in Pancreatic Islet Cells

To determine whether sequences within the 5' flanking region of the STF-1 gene were sufficient to target expression of STF-1 to pancreatic islet cells, 6500 base pairs extending from −6500 to −1 bp of 5' flanking STF-1 sequence were fused to the β-galactosidase gene and the expression this STF-1-lac z reporter was examined in transgenic mice. Using X-gal as chromogenic substrate, β-galactosidase activity was detected in pancreatic islets of transgenic, but not control littermates, from three independent founder lines (FIG. 3A).

In keeping with the previously described expression pattern for endogenous STF-1 protein, no significant β-galactosidase activity was detected in exocrine acinar cells (FIG. 3B) or in non-pancreatic tissues such as liver and spleen of transgenic mice (not shown). In keeping with the reported expression of the endogenous STF-1 gene in the duodenum (8, 13), in situ hybridization studies with antisense β-galactosidase RNA probe also revealed transgene expression in epithelial cells of the duodenum from transgenic animals (not shown). These results indicate that 6500 base pairs of the STF-1 promoter are indeed sufficient to target expression of STF-1 to pancreatic islet and duodenal cells.

Figure 4A:
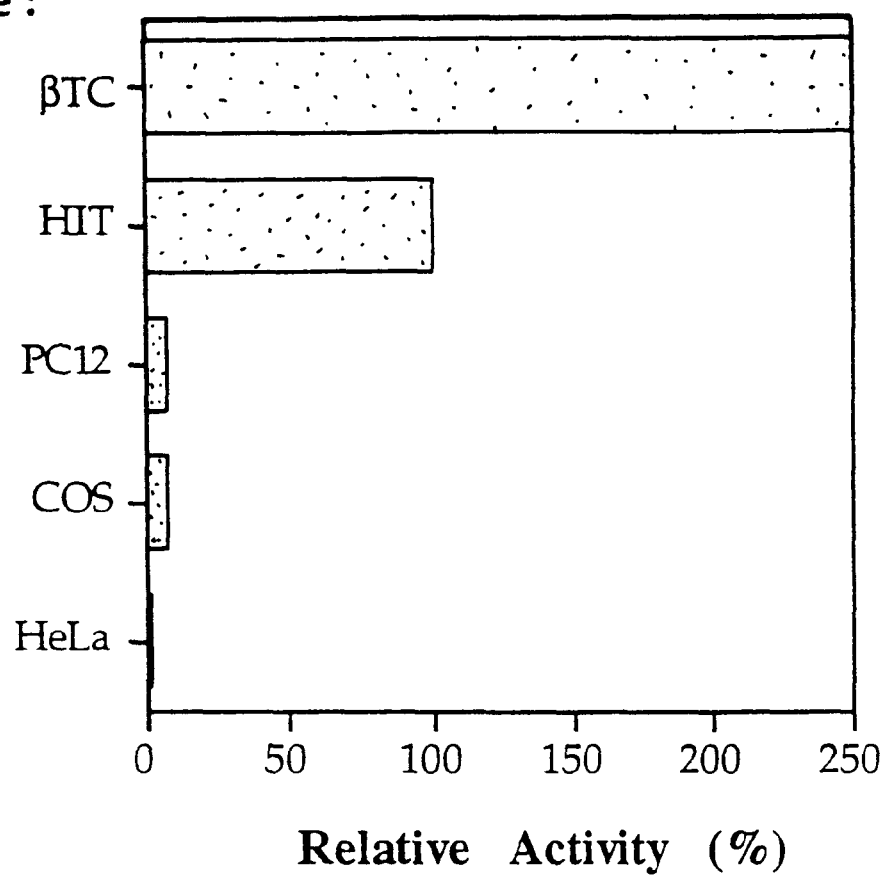
FIG. 4A shows the activity of a –6500 STF-1 luciferase reporter plasmid following transfection into pancreatic islet (βOTC 3, HIT) versus non-islet cell lines (PC12, COS, HeLa). A representative assay shows STF-1 promoter activity in HIT cells (100%) relative to other cell lines after normalization with co-transfected RSV-CAT control plasmid. Assays were repeated at least three times.

To define functional elements which direct STF-1 expression to pancreatic islet cells, the activity of the −6500 STF Luc reporter was examined in two distinct pancreatic islet cell lines (βTC 3, HIT). As predicted from results in transgenic mice, the STF-1 reporter showed 20 to 100-fold more activity in these islet cells compared to non-islet lines such as HeLa, PC12, and COS (FIG. 4A). By contrast, the 4 kilobase intron and 3 kilobase 3' flanking region of the STF-1 gene showed no such activity when inserted into a minimal SV40 CAT promoter plasmid (not shown), suggesting that the 6.5 kilobases STF-1 promoter fragment is specifically responsible for targeted expression of STF-1 in islet cells.

Figure 4B:
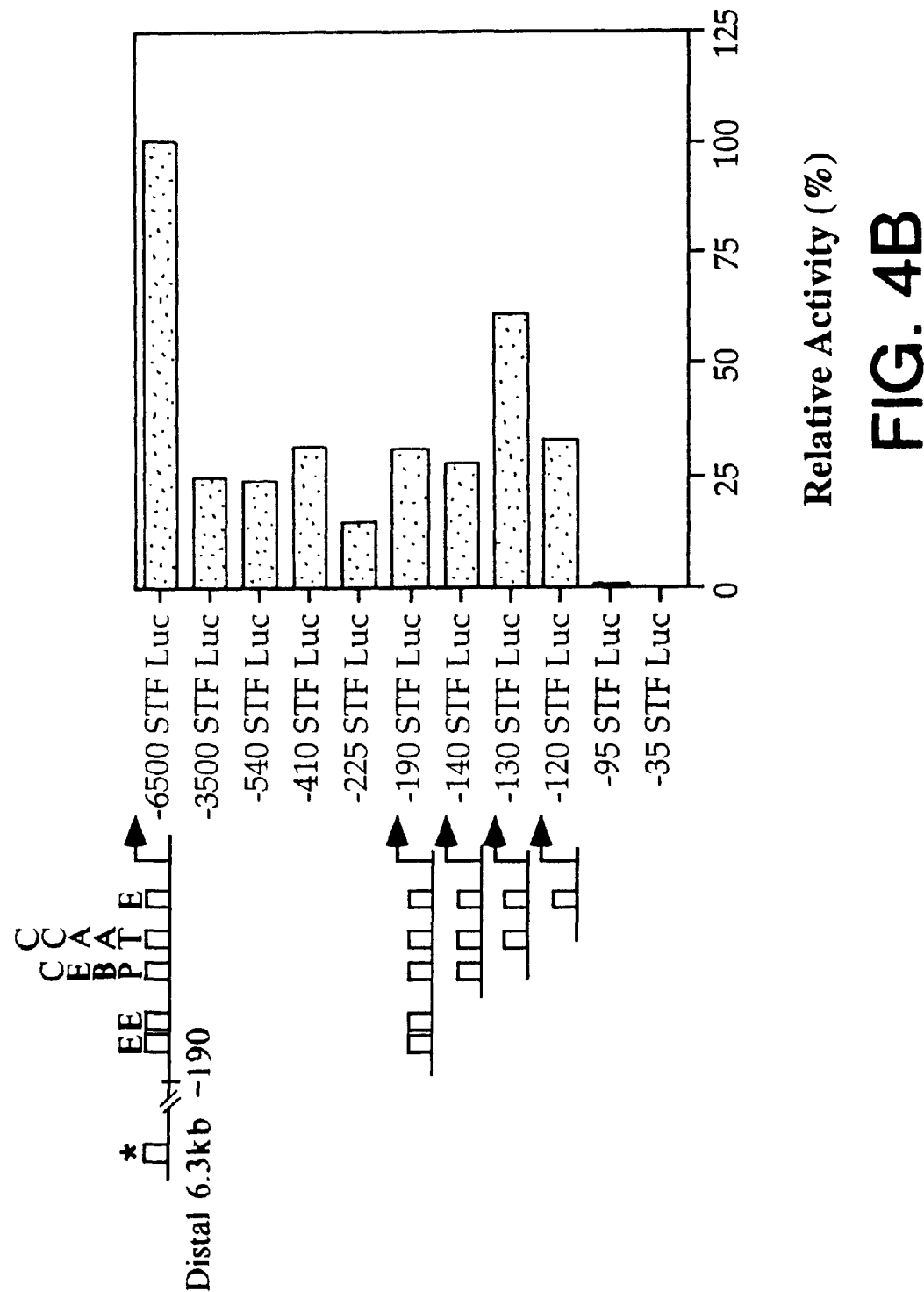
FIG. 4B shows a representative assay of STF-1 luciferase (STF luc) promoter constructs following transfection into HIT cells. Constructs were named according to the 5' promoter boundary relative to the major transcriptional start site (S1, see FIG. 2A and 2B). Schematic diagrams show the position of potential binding sites for nuclear factors; the major transcriptional start site is represented by the filled arrow. The asterisk indicates uncharacterized binding activity in the distal 3 kilobases. For each construct, activity was calculated relative to –6500 STF Luc (100%) following normalization for transfection efficiency using RSV-CAT as an internal control. Assays were repeated at least four times.

To delineate sequences within the STF-1 promoter which confer islet cell expression, a series of 5' deletion constructs were generated and these reporters were analyzed by transfection into HIT cells (FIG. 4B). Deletion of sequences from −6500 to −3500 base pairs from the −6500 STF reporter construct reduced STF-1 reporter activity four fold, suggesting the presence of a distal activating sequence within that region. Further truncation of the STF-1 promoter from −3500 base pairs to −190 base pairs did not affect reporter activity in HIT cells significantly (FIG. 4B). But deletion of STF-1 promoter sequences from −190 to −95 base pairs severely attenuated reporter activity in HIT cells, indicating that a proximal element was also required for STF-1 promoter function. Inspection of the sequence in the −190 to −95 region of the STF-1 promoter revealed three consensus E box motifs (FIG. 2A). Although removal of two tandem E boxes at −177 did not reduce promoter activity, deletion of the proximal E box sequence at −104 (−95 STF luc) completely abolished STF-1 expression in HIT cells.

EXAMPLE 10

A proximal E box in the STF-1 promoter recognizes a USF-containing complex

Figure 5A:
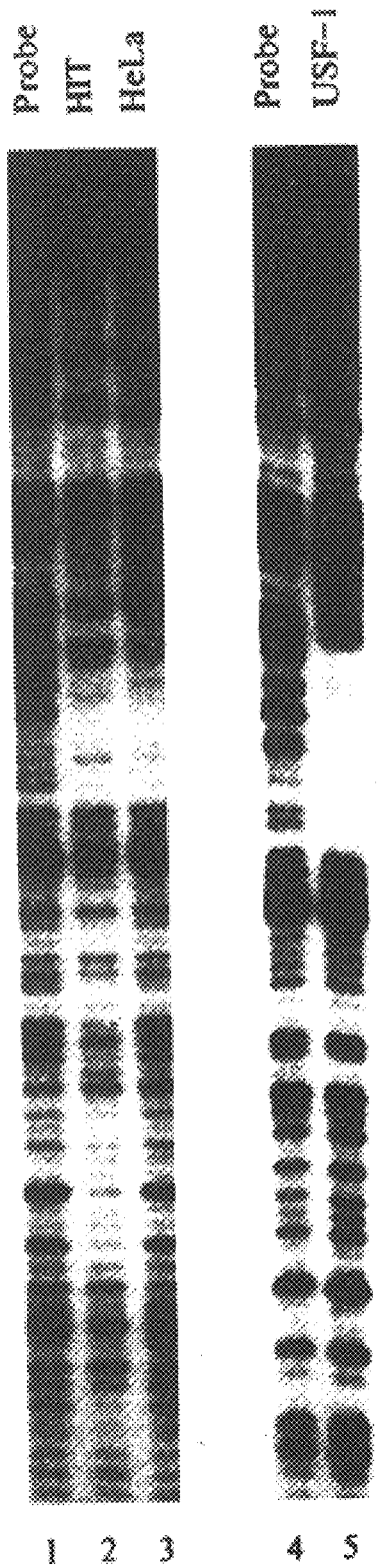
FIG. 5A shows the results of a DNase I protection assay using a $^{32}$P-labeled STF-1 promoter fragment extending from –182 to –37 (145 base pairs). The autoradiogram shows the digestion pattern with no extract (lanes 1 and 4), with nuclear extracts from HIT or Hela cells (lanes 2 and 3, respectively), or with recombinant USF-1 (lane 5).
Figure 5B:
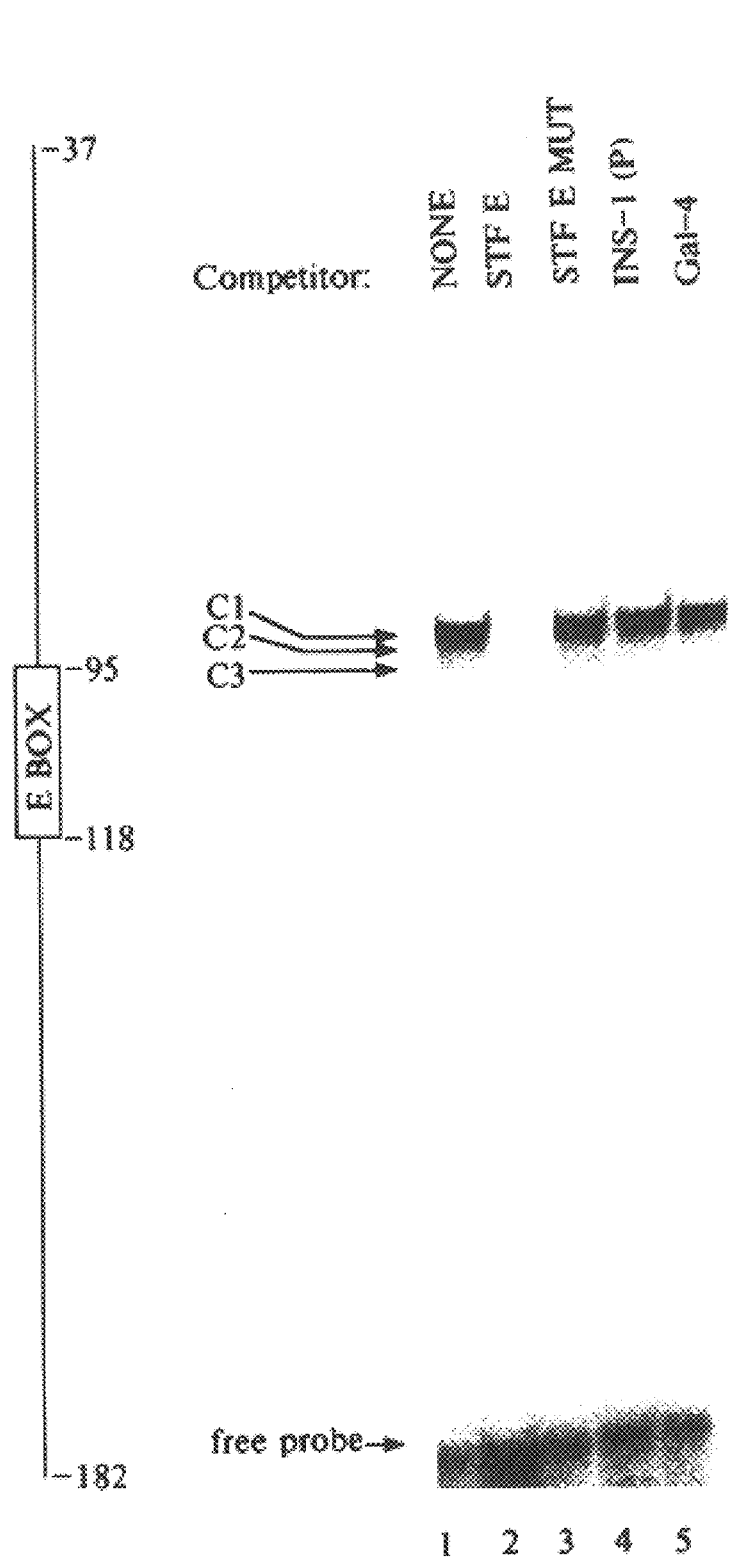
FIG. 5B shows an electrophoretic mobility shift assay of HIT nuclear extract incubated with a $^{32}$P-labeled double stranded oligonucleotide containing the STF-1 E box (–118/–95) (lane 1). Unlabeled competitor oligonucleotides (50 fold molar excess) were added to binding reactions as indicated (lanes 2–5): STF E is the wildtype STF-1 E box oligo; STF-E MUT indicates the mutant STF-E oligo containing substitutions in the E box motif at –106 (C/A) and –102 (T/G); Ins-1 (P) is the P-element from Insulin I promoter; and Gal4 indicates the GAL4 recognition site.

To characterize upstream factors which bind to functional elements in the STF-1 promoter, DNase I protection assays were performed using nuclear extracts from HIT and HeLa cells (FIG. 5A). In both extracts, a predominant footprinting activity was observed whose boundaries coincided with the functionally important proximal E box motif (−118/−95). To further characterize the proteins which bind to the critical −104 E box motif in HIT versus HeLa extracts, gel mobility shift assays were performed. Using a double stranded STF-1 oligonucleotide extending from −118 to −95, three complexes, termed C1, C2 and C3, were observed with both nuclear extracts (FIG. 5B, right panel, lanes 1 and 4). Formation of C1, C2, and C3 complexes was inhibited by a 50 fold excess of unlabeled STF-1 E box competitor oligonucleotide in binding reactions. Mutant E box oligonucleotide or nonspecific competitor DNAs had no effect on these binding activities, however, indicating that C1, C2, and C3 are indeed specific for the STF-1 E-box sequence (FIG. 5B). No qualitative difference in the pattern of these complexes was detected between Hela and HIT extracts (not shown), suggesting that the −104 E box motif may recognize factors which are comparably expressed in both cell types.

Figures 5C, 5D:
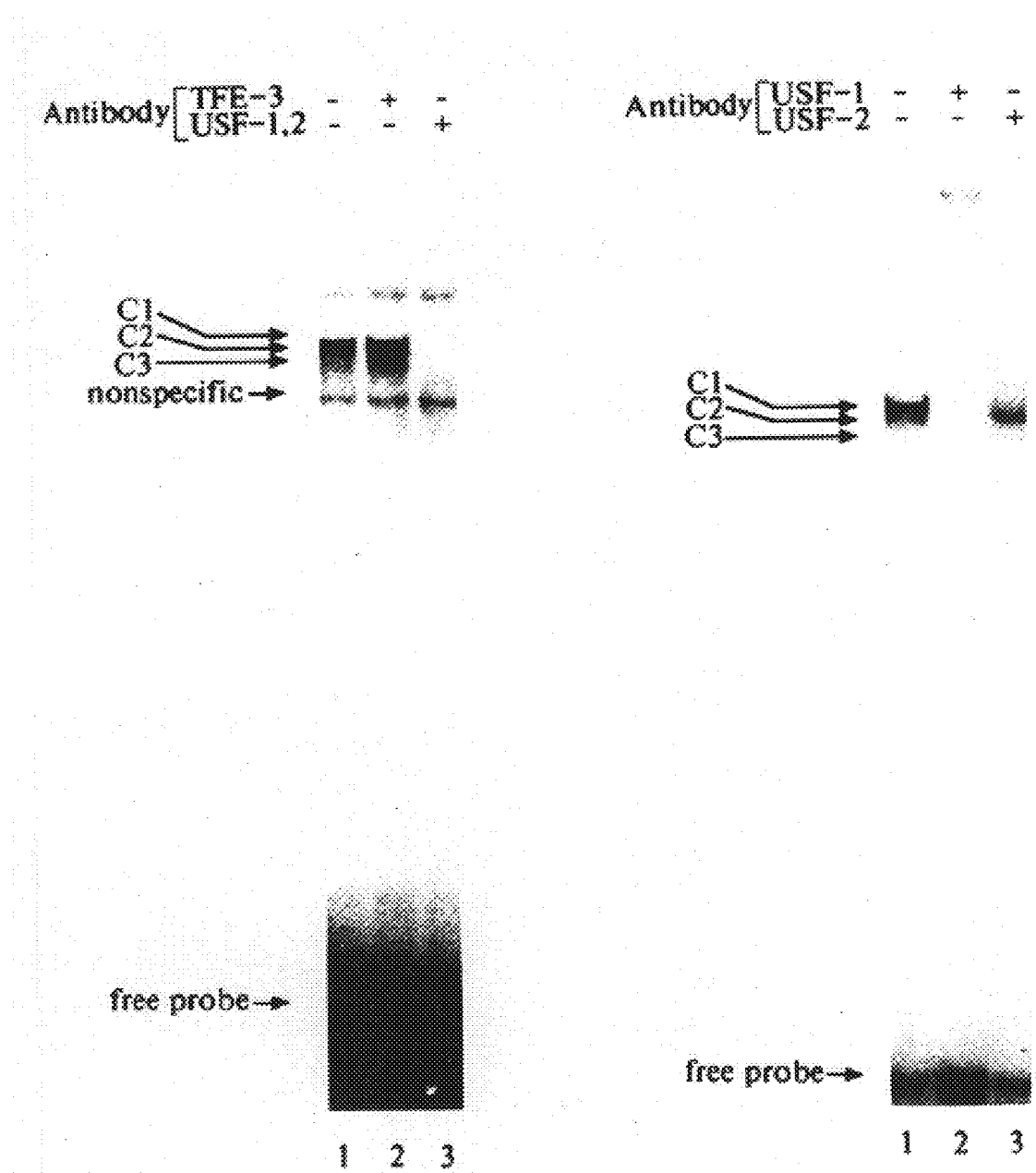
FIG. 5C, shows the results of a gel shift assay of HIT nuclear extracts using STF-E box as probe (lane 1). Addition of USF or TFE-3 antibody to the reactions is as indicated (lanes 2 and 3). Complexes C1, C2, C3, are as labeled.
FIG. 5D shows the results of a gel shift assay of HIT (lanes 1–3) extracts using STF-E robe. The addition of USF-1 and USF-2 specific antisera to the inding reactions is indicated.

Previous reports demonstrated that E boxes like the −118/−95 STF-1 motif (CACGTG) preferentially bind bHLH-ZIP proteins such as myc, max, TFE-3, TFE-B, and USF. Whether any of these candidate proteins was contained within the C1, C2, or C3 complexes (26, 27) was determined. The ability of the −118/−95 E box binding protein to withstand heat denaturation (not shown) led to the examination of whether USF, a heat stable upstream factor, was a component of C1, C2, or C3 (28). Remarkably, addition of anti-USF antiserum to gel mobility shift reactions inhibited formation of all three complexes (FIG. 5C). But anti-TFE-3 antiserum had no effect on complexes C1, C2, or C3, suggesting that these complexes were most likely formed by USF proteins. In gel shift assays, recombinant USF-1 gave rise to a protein DNA complex which migrated at the same relative position as complex C2 (not shown). And in DNase I protection studies, recombinant USF-1 footprinting activity coincided with that observed in HIT extracts (FIG. 5A).

Two forms of USF, termed USF-1 and USF-2, appear to be expressed in most cell types (18). To distinguish which of these USF proteins was contained within the C1, C2, and C3 complexes, a HIT or HeLa extract was incubated with either anti-USF-1 specific or anti-USF-2 specific antiserum (FIG. 5D). Although USF-1 antiserum could "supershift" all three complexes, the USF-2 specific antiserum only inhibited formation of the C1 and C3 complexes. These results suggest that complexes C1 and C3 correspond to USF-1/USF-2 heterodimers whereas C2 may contain a USF-1 homodimer.

Figure 6A:
FIG. 6A shows the effect of E-box mutations on USF-binding activity. The results of a gel shift assay of HIT nuclear extract using wild-type (E-WT) or mutant (E-MUT) STF-1 E box probes is shown with the sequence of wild-type and mutant probes from −106 to −102 shown below. C1–3, complexes C1, C2, and C3.
Figure 6A:
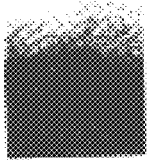
Figure 6B:
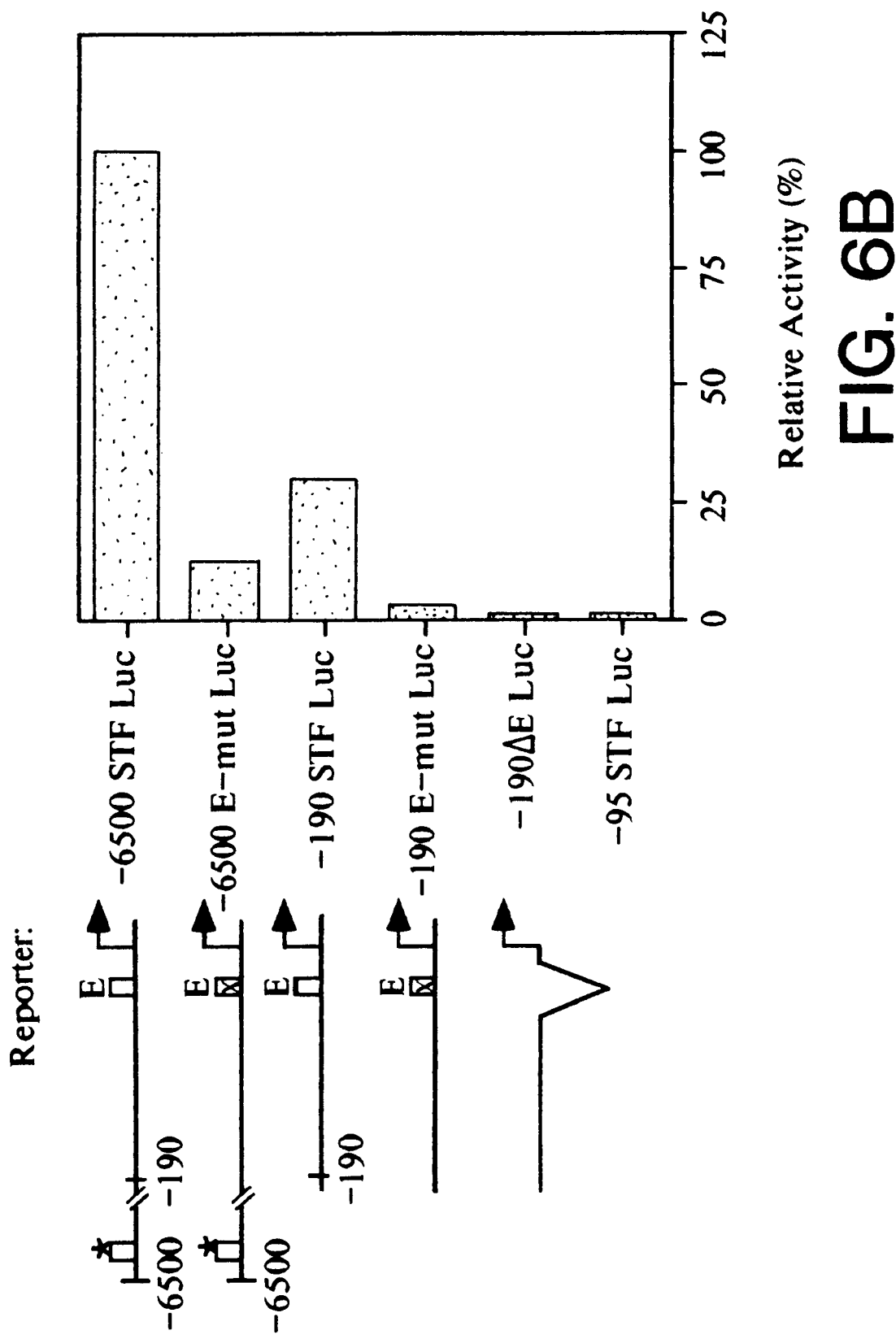
FIG. 6B shows the effect of E-box mutations on STF-1 promoter activity in HIT cells. Shown is a representative assay of HIT cells transfected with wild type, mutant, or deleted (−118/−95) STF-1 E box motifs in the context of 6500 base pairs or 190 base pairs of STF-1 promoter. Reporter activities are shown relative to wild-type −6500 STF-1 Luc (100%) construct after normalizing for transfection efficiency with a co-transfected RSV-CAT control plasmid. Assays were repeated at least three times.

To verify whether the CACGTG E box sequence was essential for STF-1 promoter activity, a mutant STF-1 oligonucleotide was constructed which contains two base pair substitutions in the E box (−118/−95). In gel mobility shift assays with HIT nuclear extracts, this mutant E box motif (AACGCG) could not form C1, C2, and C3 complexes and could not compete for binding of USF-1 to wild-type E box oligonucleotide (FIG. 6A). Correspondingly, full-length (6.5 kilobases) STF-1 and truncated (−190 STF) reporter plasmids containing the mutant STF E motif were nearly 10 fold less active than their wild-type counterparts in pancreatic islet cells (FIG. 6B). These results demonstrate that the proximal E box which binds USF is indeed critical for STF-1 promoter activity.

Thus, two elements within the first 6500 base pairs of STF-1 5' sequence appear to be important for islet-specific expression: a distal element located between −6500 to −3500, and a proximal element located at −104. The proximal −104 element consists of a consensus E-box motif which recognizes the upstream activator USF. Multiple lines of evidence suggest that USF is important for STF-1 promoter activity. First, both nondiscriminating USF-1,2 antibodies as well as USF-1 and USF-2 specific antibodies recognize the complexes specific for the STF-1 E box. Secondly, the STF-1 E box binding activity in HIT nuclear extracts has characteristics reminiscent of USF: the complexes are heat stable and demonstrate half lives similar to recombinant USF-1. Finally, point mutations which inhibit formation of USF complexes on the STF E box correspondingly attenuate STF-1 reporter activity. These results suggest that USF complexes are indeed important for STF-1 promoter activity and consequently for pancreatic organogenesis.

Other nuclear factors in addition to USF, most notably myc and max, can also bind with high affinity to the STF-1 E box (CACGTG) motif. Myc has been shown to stimulate target gene transcription by binding as a heterodimer with max to E-box motifs (32, 33). As myc gene expression is typically undetectable in postmitotic cells such as those in pancreatic islets, myc-max complexes may not be involved in STF-1 promoter regulation there. During development, however, STF-1 expression appears to be concentrated in proliferating ductal cells (6), and myc may consequently stimulate STF-1 expression under those conditions. In this regard, the profound changes in STF-1 expression which are observed during pancreatic development may in part reflect changes in E-box binding activities which ultimately restrict STF-1 production to pancreatic islet cells.

EXAMPLE 11

Gel shift assays and DNase I protection assays.

For electrophoretic mobility shift assays, double stranded oligonucleotides were labeled using $^{32}$PdCTP fill-in reaction with Klenow fragment. Five micrograms of nuclear extract was incubated with 0.5 ng of labeled oligonucleotide and 1 μg of nonspecific competitor DNA for 30 minutes on ice and subjected to nondenaturing polyacrylamide electrophoresis. For supershift assays, nuclear extracts were pre-incubated with antiserum for 30 minutes to 1 hour on ice prior to addition of labeled probe. Anti-HNF-3α, HNF-3β, and HNF-3γ antibodies were kindly provided by S. Duncan and J. Darnell. Anti-BETA-2 antibody was a generous gift of M. J. Tsai. Anti-E2A antibody was purchased from Santa Cruz Biochemicals. DNAse I protection assays were performed as previously described (37). Recombinant HNF-3α was the gift of K Zaret.

EXAMPLE 12

Northern blotting.

Somatostatinoma/insulinoma Tu6 cells were cultured in ethanol or $10^{-7}$ dexamethasone for varying amounts of time. Total RNA was extracted using a guanidinium-phenol procedure. Fifteen micrograms of total RNA was run on agarose gels containing formaldehyde and transferred to Zeta-Probe. Random primed STF-1 and tubulin cDNAs were generated using the Amersham random priming kit.

EXAMPLE 13

Figure 7B:
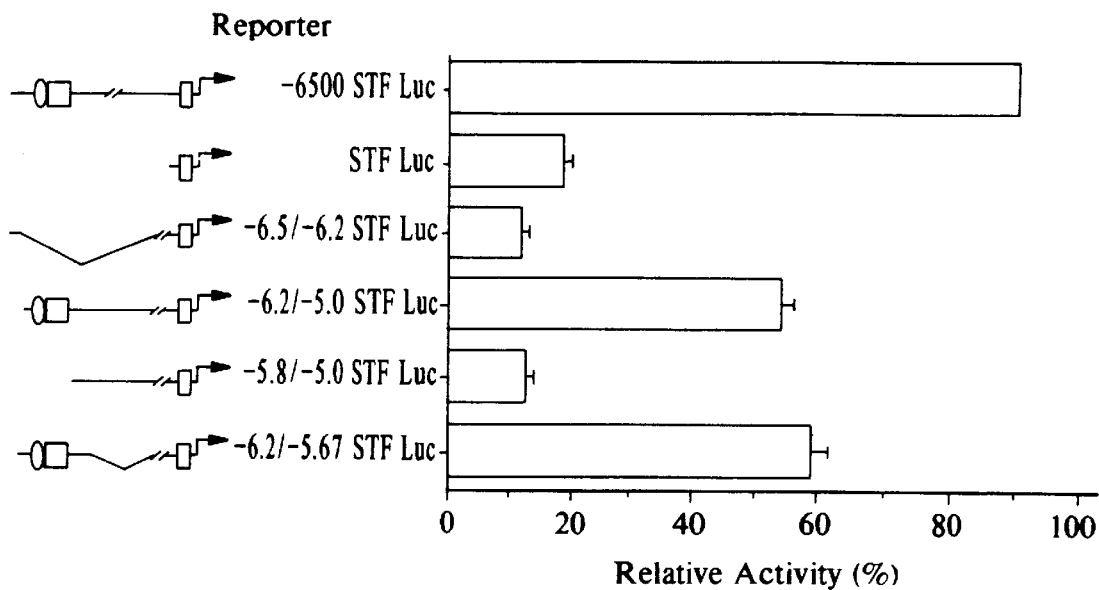
FIG. 7B (Top) shows the results of a transient transfection assay of STF-1 reporter constructs in HIT T15 cells. The activity of −6500 STF Luc, which contains 6500 bases of 5' flanking sequence set at 100%. Each assay was repeated in duplicate at least four times. Standard errors are as shown. (Bottom) The activity of STF-1 luciferase reporter plasmids following transient transfection into COS-7 cells is shown. Promoter activity is normalized to CMV-βgal control activity, allowing for direct comparison with STF-reporter activity in HIT cells.
Figure 7B:
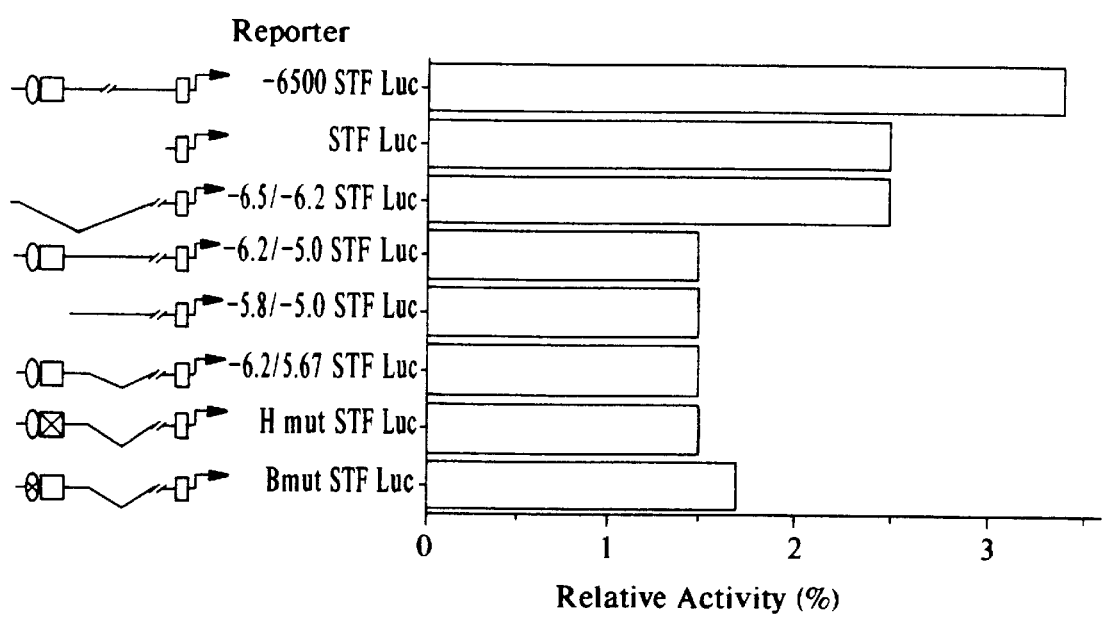

The Endodermal Factors HNF-3β and BETA-2 Regulate STF-1 Expression via an Islet Specific Enhancer Promoter constructs containing a 530 base pair fragment extending from −6200 to −5670 of the STF-1 gene were fully repressed by dexamethasone treatment, but a minimal STF-1 promoter construct containing the ubiquitous USF-1 recognition site was not (FIG. 7a). The same 530 bp region of the STF-1 gene was about 5–10 fold more active in HIT-T15 cells compared to COS-7 cells, demonstrating that this fragment contains islet cell specific activity (FIG. 7b). Inspection of the nucleotide sequence within the cell specific STF-1 enhancer revealed consensus motifs for E-box binding proteins (−5.98 to −5.963 kb relative to the major transcription initiation site of STF-1) and for HNF-3 (−5.927 to −5.907 kb relative to the major transcription initiation site of STF-1) (FIG. 7c). The E box motif, termed the B element, is identical in sequence to that of the NIR and FAR elements within the rat insulin I and II promoters (34). And the HNF-3 site, referred to as the H element, coincides with the HNF-3 consensus binding site in 9 of 12 positions (35).

Figure 8A:
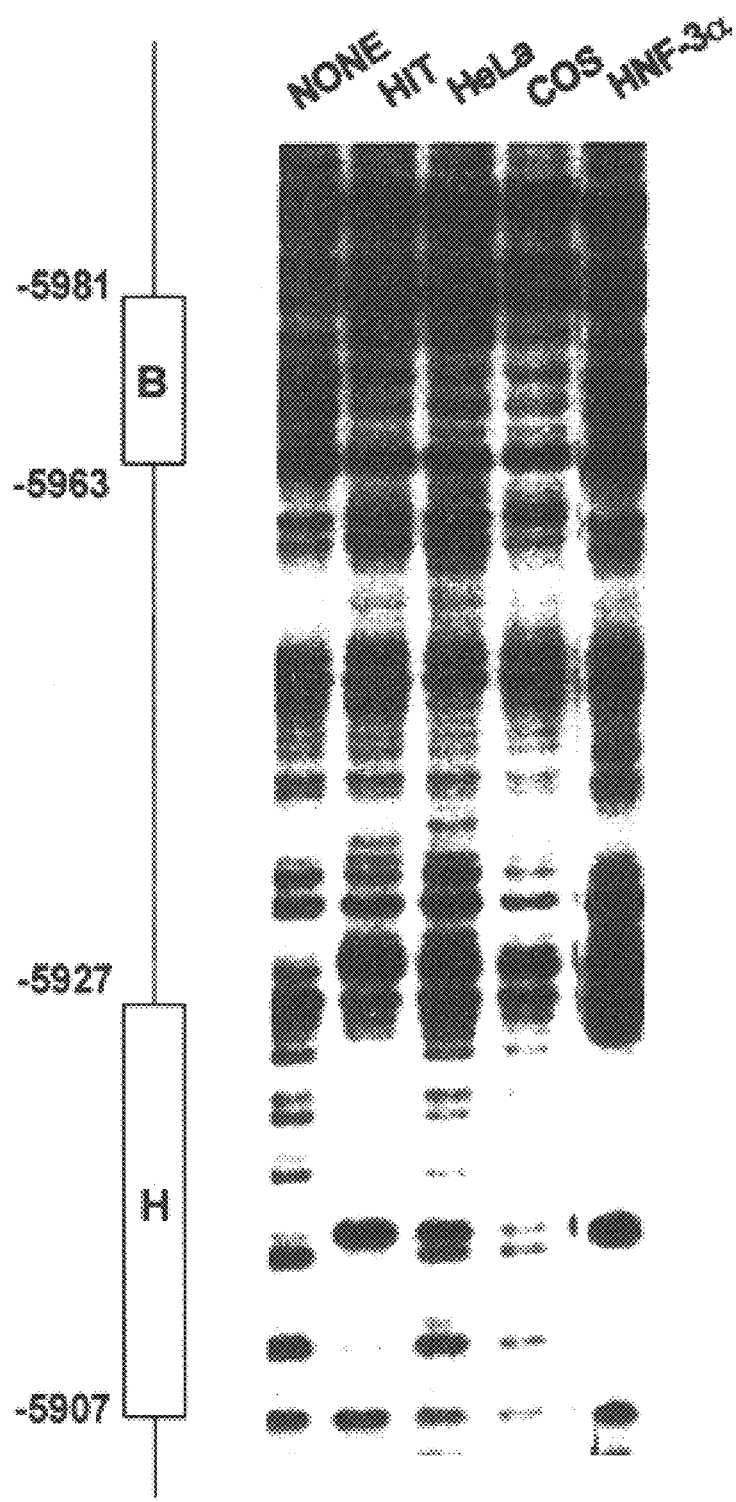
FIG. 8A shows the results of DNAse I protection assays of crude nuclear extracts from HIT T15 islet cells, Hela, or COS-7 cells, using $^{32}$p-labeled STF-1 probe extending from −5870 to −6100 of the rat STF-1 promoter. NONE; control reaction without added extract; HNF-3α; reaction using recombinant protein.

To determine whether the B and H elements are indeed recognized by islet specific nuclear proteins, we performed DNAse I protection assays using a $^{32}$P-labeled STF-1 enhancer fragment extending from −5870 to −6100. Nuclear extracts prepared from HIT T15 cells were found to contain DNA binding activities over both the B (E-box motif) and H (HNF-3 motif) sites (FIG. 8a, compare lanes 1 and 2). The B element was comparably protected in DNAse I protection assays with nuclear extracts from HIT, Hela and COS 7 cells, whereas protection of the H element was only observed with extracts from HIT cells (FIG. 8a, compare lanes 2 and 4). A prominent hypersensitive site which interrupted the H element footprint was also noted in reactions containing purified recombinant HNF-3α protein, leading us to speculate that a member of the HNF-3 family of regulators binds to the STF-1 H element in HIT-T15 cells (FIG. 8a, compare lanes 2 and 5).

Figure 8B:
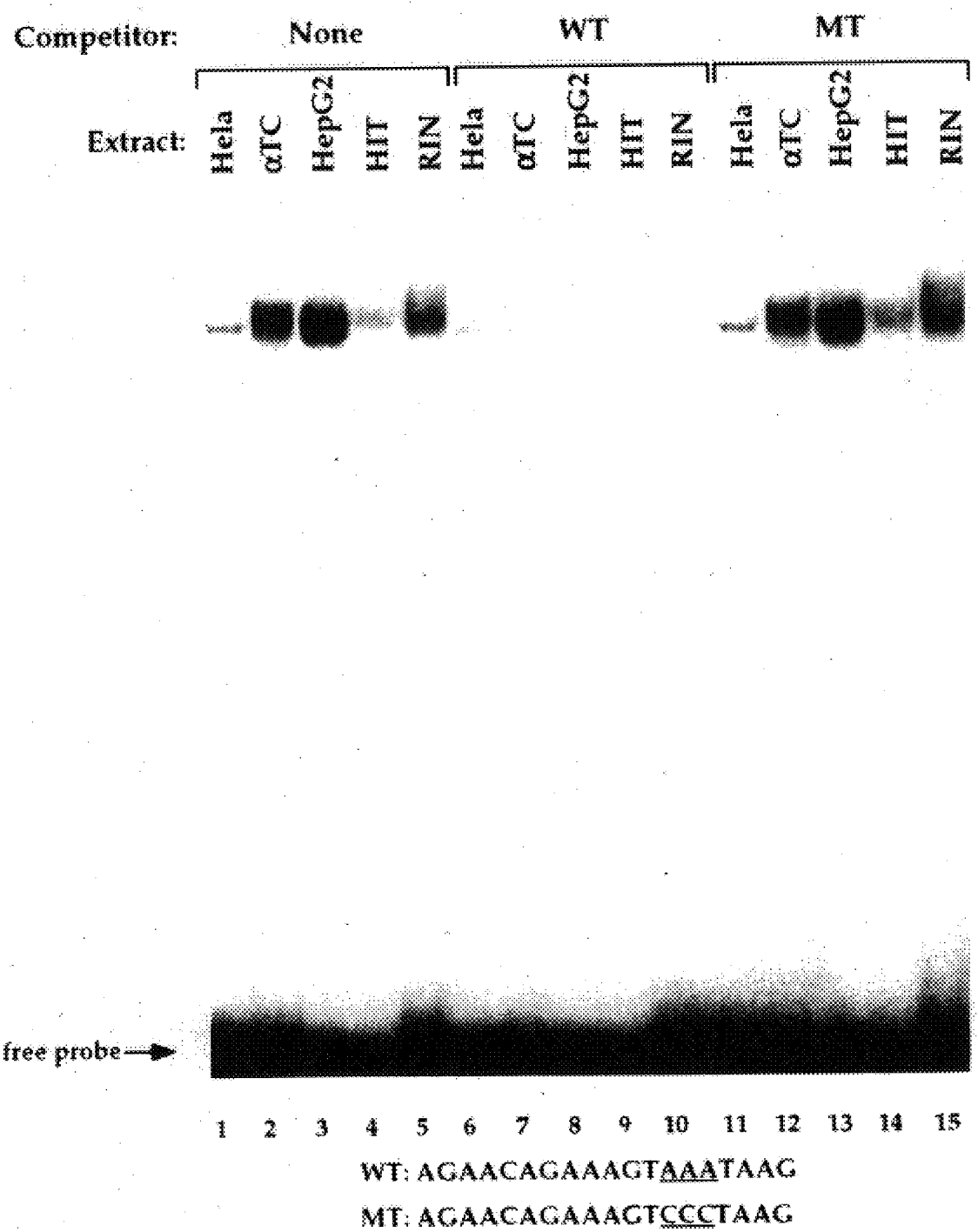
FIG. 8B shows the results of a gel mobility shift assay of crude nuclear extracts from Hela, HepG2, glucagon producing αTC, or insulin producing HIT and RIN cell lines, as indicated over each lane. Assays were performed with $^{32}$P-labeled STF-1 oligonucleotide robe containing the H element. Nucleotide sequence of wild-type (WT) and mutant (MT) H elements shown below. Addition of 100-fold excess of unlabeled wild-type or mutant competitor DNA as indicated over lanes.

To further characterize nuclear factors which recognize the H element on the STF-1 enhancer, we performed gel mobility shift assays using a $^{32}$P-labeled STF-1 H element probe. One major low mobility complex was observed in reactions containing HIT or RIN nuclear extracts, and formation of this complex was specifically inhibited by adding 100-fold molar excess of unlabeled wild-type but not mutant H element competitor DNA (FIG. 8b, compare lanes 4–5, 9–10, 14–15). No specific protein DNA complexes were observed in reactions containing Hela nuclear extracts, indicating that the H element may recognize nuclear factors with a restricted expression pattern (FIG. 8b, compare lanes 1,6).

The presence of an H-element specific complex in HepG2 hepatoma extracts running at the same mobility as the RIN/HIT-T15 complex, however, suggested that the H-element binding protein may be generally expressed in cells of endodermal origin (FIG. 8b, compare lanes 3–5).

Figure 8C:
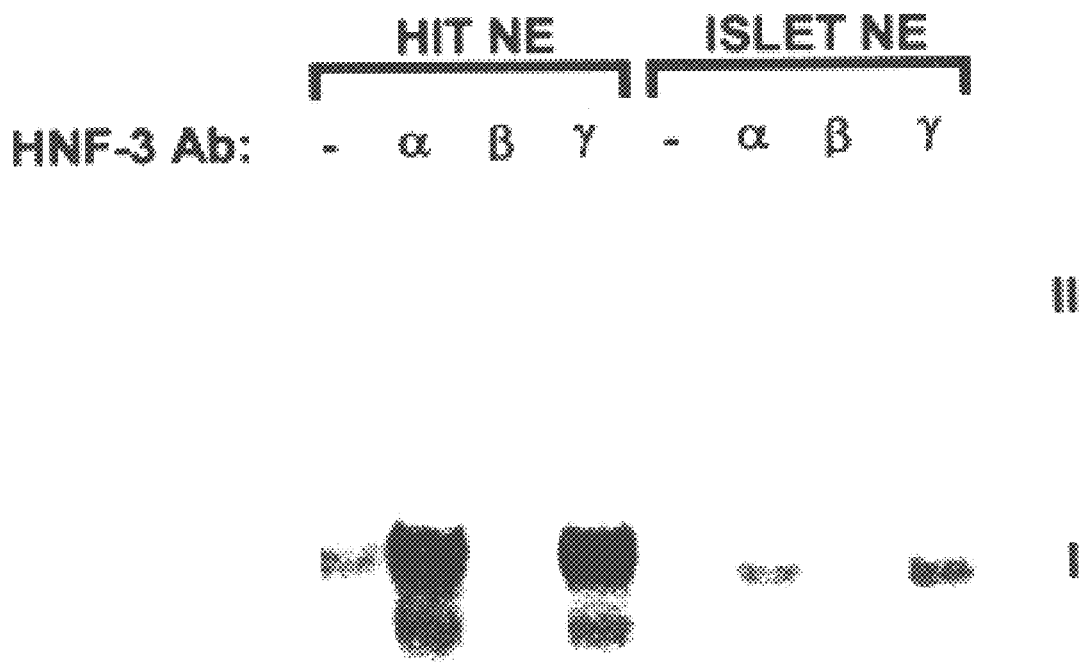
FIG. 8C shows the results of a gel mobility shift assay of crude nuclear extract from HIT insulinoma (HIT NE) and primary cultured adult rat islet cells (ISLET NE) using $^{32}$P-labeled STF-1 H element probe extending from −5907 to −5927. Addition of HNF3 α, β, or γ antisera to reactions is as is indicated over each lane. -; no antiserum added. I and II, protein-DNA and antibody supershifted complexes, respectively.

The HNF-3 family of nuclear activators consists of three genes ($\alpha,\beta$, and $\gamma$) which bind to DNA via a highly conserved winged helix domain (36). To determine whether the H-element binding activity in HIT extracts corresponded to an HNF-3 family member, we performed gel mobility shift studies using specific antisera against each of the HNF-3 members. Although each of the three HNF-3 proteins was detected in nuclear extracts of HIT-T15 insulinoma cells by Western blot analysis (not shown), only HNF-3$\beta$ antiserum was found to block formation of the major protein-DNA complex using the same extract with an H-element probe (FIG. 8c, lanes 1–4). Identical results were obtained in gel shift assays of nuclear extracts prepared from primary cultures of adult rat islet cells (FIG. 8c, lanes 5–8).

Figure 8D:
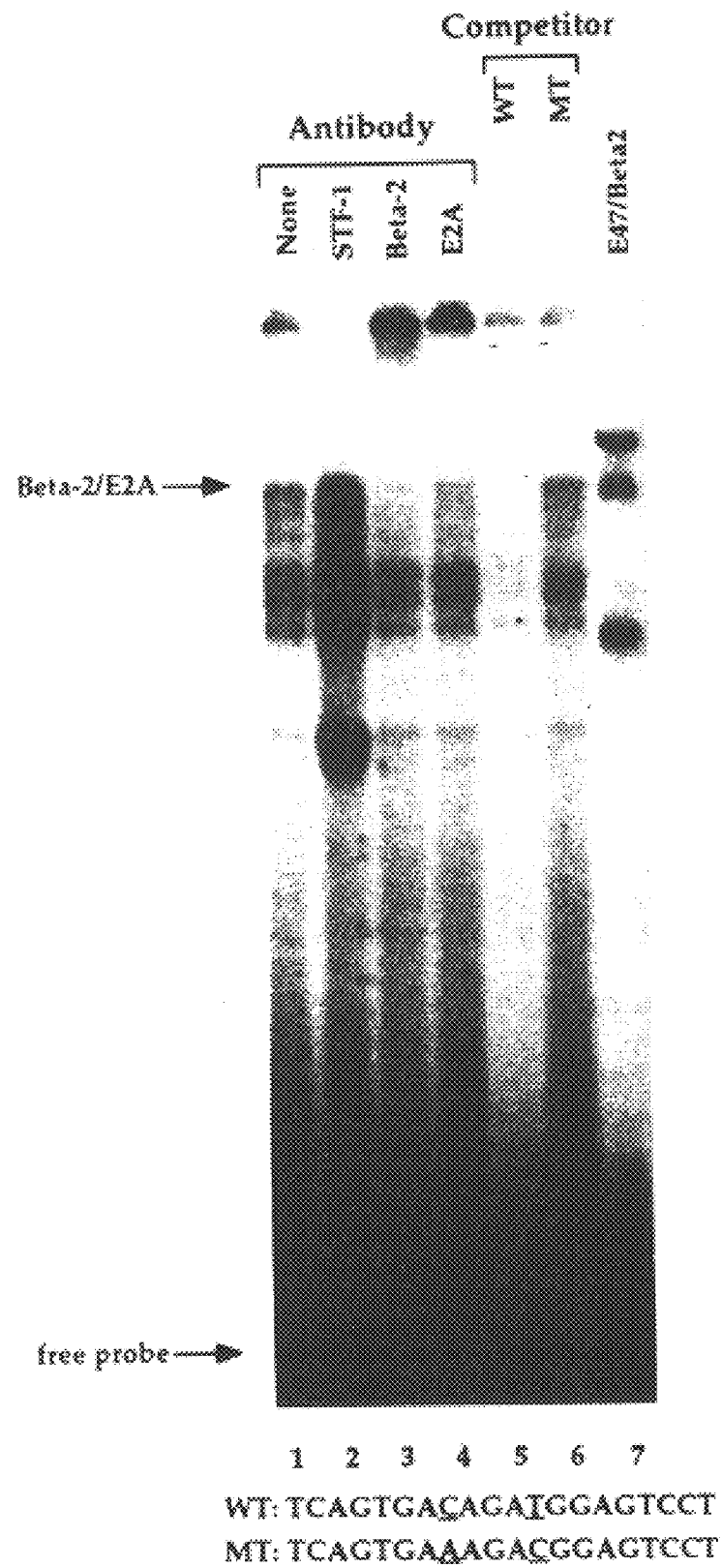
FIG. 8D shows the results of a gel mobility shift assay of crude nuclear extract from HIT T15 cells using $^{32}$P-labeled B-element probe extending from −5963 to −5981 of the STF-1 promoter. Addition of BETA-2, E2A, or STF-1 antiserum to binding reactions is indicated over each lane. Addition of 100-fold excess of unlabeled wild-type (WT: 5'-TCAGTGACAGATGGAGTCCT-3') or mutant (MT: 5'-TCAGTGAAAGACGGAGTCCT-3') competitor DNA as indicated. Binding activity derived from reticulocyte lysate programmed with BETA-2 and E-47 cDNAs is shown in lane 7. The top band in lane 7 is indigenous to retulocyte lysate.

The B-element within the STF-1 enhancer contains a consensus E-box motif which is identical to E box elements within the insulin promoter(33). Previous work demonstrating that the islet-specific factor BETA-2 activates insulin promoter activity by binding to these insulin promoter elements as a heterodimer with the ubiquitous factor E47 (14), prompted us to test for BETA-2/E47 heterodimer formation on the STF-1 B element. In gel mobility shift assays of HIT nuclear extracts, a $^{32}$P-labeled B element probe was observed to form four specific DNA protein complexes which could be competed by addition of unlabeled wild-type but not a mutant B-element oligonucleotides (FIG. 8d, compare lanes 1, 5, 6). The slowest complex migrated at the same position as recombinant E2A/BETA2 heterodimeric complex (FIG. 8d, compare lanes 1 and 7). Although an unrelated antiserum had no effect on B element binding activities (FIG. 8d, lane 4), BETA-2 or E2A antisera specifically inhibited formation of the slowest complex (FIG. 8d, lanes 2 and 3), revealing that the BETA-2/E47 heterodimer does indeed recognize the B element in HIT nuclear extracts.

Figure 9A:
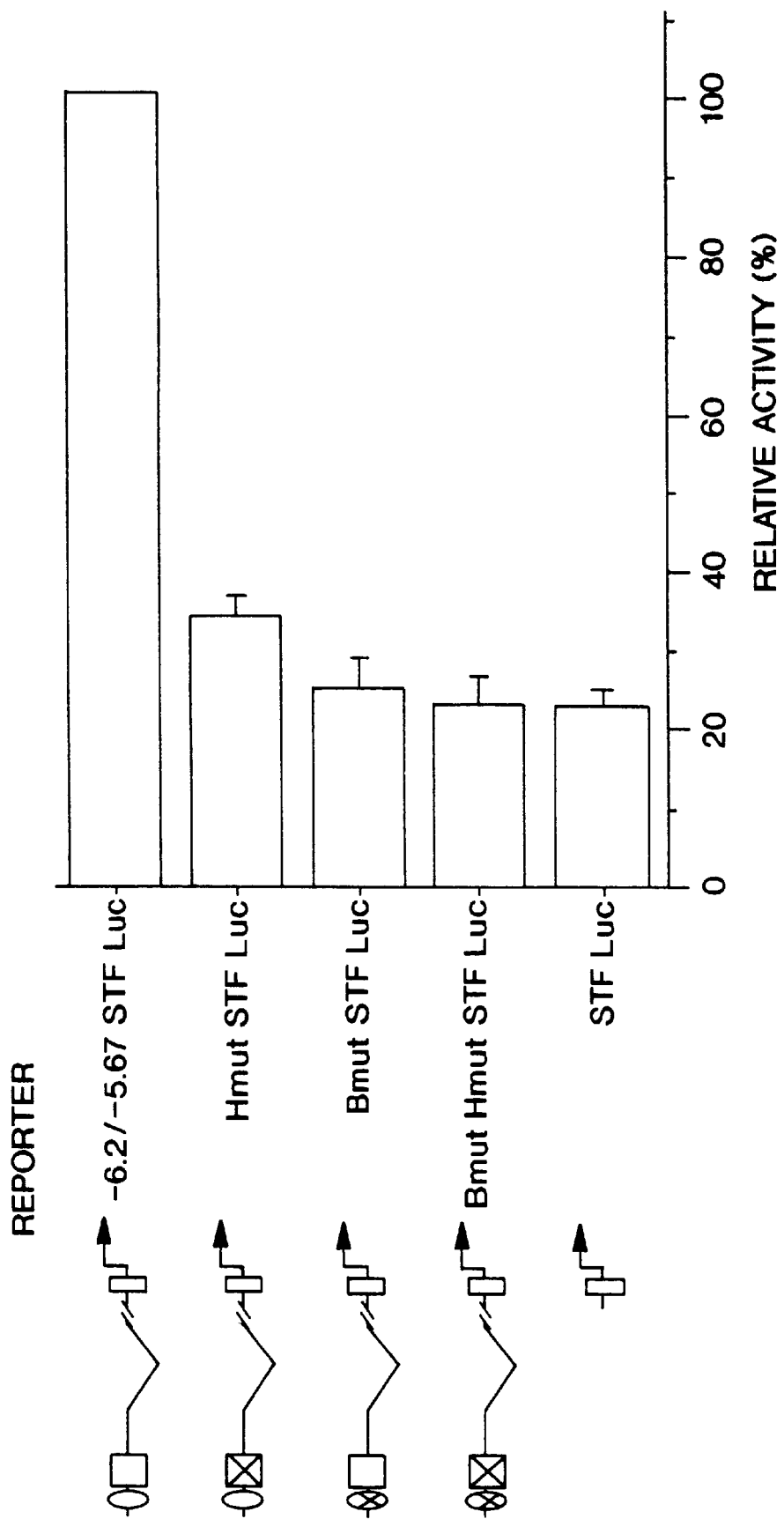
FIGS. 9A (A–C) shows the results of a transient transfection assay of STF-1 reporter plasmids in HIT T15 insulinoma cells. The activity of the −6.2/−5.7 STF Luc construct containing minimal islet specific enhancer (−6200 to −5700) is set at 100%. Constructs containing point mutations in H and B elements which disrupt binding of HNF-3β and BETA2/E2A are designated by X in an oval or square. Point mutations correspond to E-box and H element mutations used in gel mobility shift assays (see FIG. 8).

To assess the importance of the HNF-3$\beta$ and E2A/BETA-2 recognition sites in mediating STF-1 enhancer activity, we generated point mutations in the B and H elements which disrupted binding of these cognate factors in vitro. When tested in the context of the 530 bp enhancer, STF-1 reporter plasmids containing mutations in either the B or H elements were much less active in HIT T15 cells relative to the wild type construct (FIG. 9a). By contrast, mutant B and H element constructs were equally active with the wild-type −6500 STF-1 reporter in COS-7 cells; however, revealing these mutations disrupt transcriptional activities which are specifically associated with islet cells. Correspondingly, B and H element mutant STF-1 reporter plasmids were also unresponsive to dexamethasone induction in HIT- T15 cells, indicating that this hormone may specifically interfere with either E2A/BETA 2 or HNF-3$\beta$ activities (FIG. 9b).

Figure 9C:
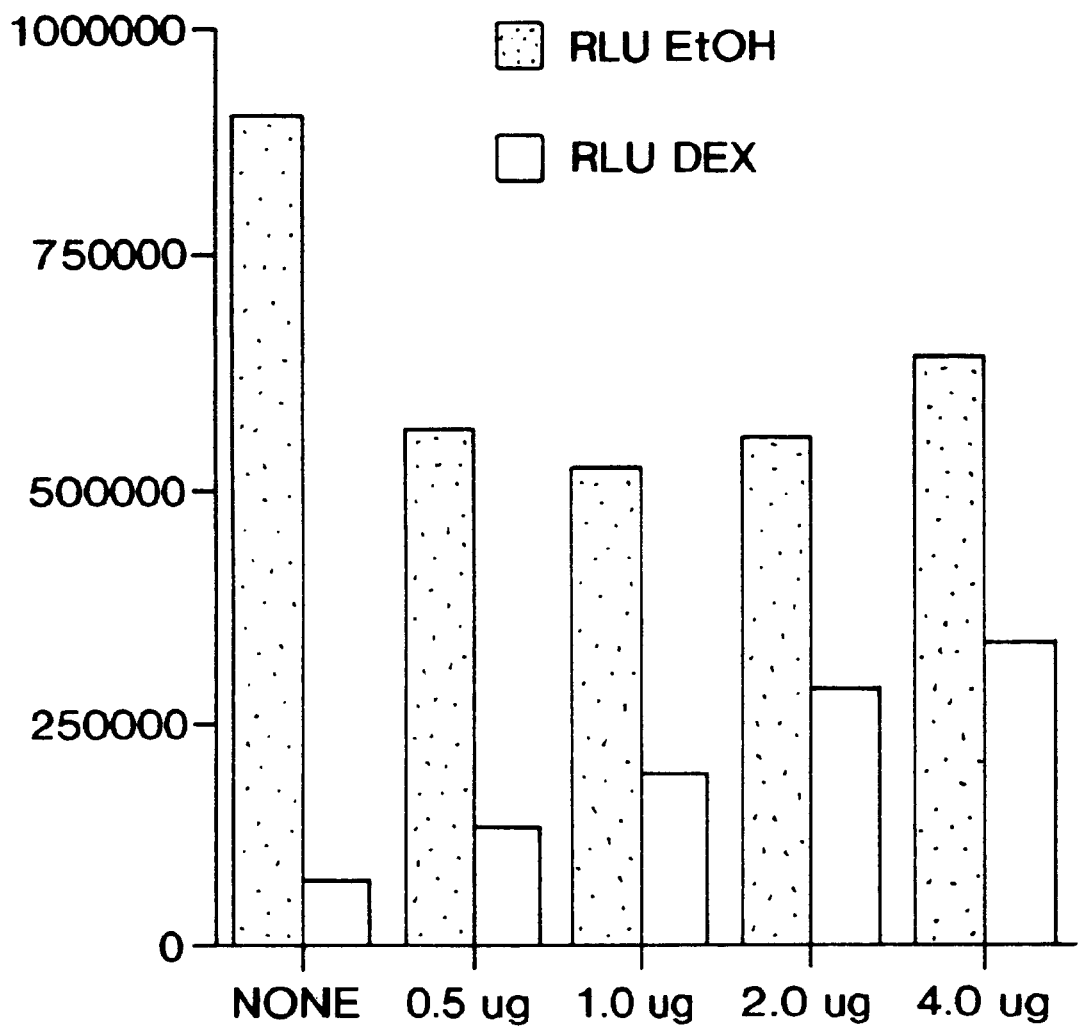
FIG. 9C shows the effect of increasing levels of HNF-3β effector plasmid on wild-type STF-1 (−6500 STF-1 LUC) reporter activity in HIT-T15 cells. The amount of HNF-3β effector plasmid (in µg) is indicated below each bar. The total amount of effector plasmid in each assay was kept constant by balancing with empty CMV expression vector. Control (ETOH) and Dexamethasone (DEX) treated cells as indicated

To evaluate whether dexamethasone inhibits STF-1 expression by disrupting HNF-3$\beta$ or BETA2/E47 activity on the distal enhancer, transient transfection assays were performed with HNF-3$\beta$ or BETA-2 and E47 effector plasmids. Over-expression of either HNF-3$\beta$ (FIG. 9b) or BETA-2/E47 (not shown) had minimal effects on STF-1 reporter expression in unstimulated HIT- T15 cells (FIG. 9b, compare bars 1 and 5). HNF-3$\beta$ was found to suppress the inhibitory effects of dexamethasone on wild-type STF-1 reporter activity (FIG. 9b, compare bars 1,3,7), but activators such as BETA-2/E47, STF-1, and HNF-4 did not rescue STF-1 promoter activity in dexamethasone treated cells (not shown). In titration experiments with increasing amounts of effector plasmid, HNF-3$\beta$ was found to rescue −6500 STF-1 LUC reporter activity in a dose-dependent manner (FIG. 9c). HNF-3$\beta$ did not potentiate the activity of a mutant STF-1 reporter plasmid containing a mutation in the H element, however, suggesting that the suppressive effects of this activator occurred via its recognition site in the STF-1 enhancer (FIG. 9b, compare bars 2,4,6,8).

The following references were cited herein.

1. Pictet, R. L., et al., *Develop. Biol.*; 29, 436–467, (1972).
2. Gittes, G. K., et al.,*Proc. Natl. Acad. Sci.*; 89, 1128–1132, (1992).
3. Alpert, S., et al., *Cell*; 53, 295–308, (1988).
4. Jonsson, J., et al., *Nature*; 371, 606–609, (1994).
5. Ohlsson, H., et al., *EMBO J.*; 12, 4251–4259, (1993).
6. Guz, Y., et al., *Development*; 121, 11–18, (1995).
7. Leonard, J., et al., *Proc. Natl. Acad. Sci.*; 89, 6247–6251, (1992).
8. Leonard, J., et al.,*Mol Endocrinol*; 7, 1275–1283, (1993).
9. Peers, B., et al., *Mol. Endocrinol.*; 8, 1798–1806, (1994).
10. Walker, M. D., et al., *Nature*; 306, 557–561, (1983).
11. Vallejo, M., et al., *J. Biol. Chem.*; 267, 12868–12875, (1992).
12. Karlsson, O., et al., *Proc. Natl. Acad. Sci.*; 84, 8819–8823, (1987).
13. Miller, C., et al., *EMBO J.*; 13, 1145–1156, (1994).
14. Naya, F. J., et al., *Genes and Dev.*; 9, 1009–1019, (1995).
15. German, M., et al., *Genes Dev.*; 6, 2165–2176, (1992).
16. Peshavaria, M., et al., *Mol Endocrinol.*; 8, 806–816, (1994).
17. VanDyke, M. W., et al., *Gene III*; 99–104, (1992).
18. Sirito, M., et al., *Nucleic Acids Res.*; 22, 427–433, (1994).
19. Madsen, O. D., et al., *J. Cell Biol.*; 103, 2025–2034, (1986).
20. Maxwell, I. H., et al.,*Biotechniques*; 7, 276–280, (1989).
21. Hanahan, D., *Nature*; 315, 115–122, (1985).
22. Montminy, M. R., et al., *Nature*; 328, 175–178, (1987).
23. Weis, L., et al., *FASEB J.*; 6, 3300–3309, (1992).
24. Ishi, S., et al., *Science*; 230, 1378–1381, (1985).
25. Geng, Y., et al.,*Mol. Cell. Biol.*; 13, 4894–4903, (1993).
26. Beckmann, H., et al., *Genes and Dev.*; 4, 167–179, (1990).
27. Gregor, P. D., et al., *Genes and Dev.*; 4, 1730–1740, (1990).
28. Sawadogo, M., et al.,*J. Biol. Chem.*; 263, 11985–11993, (1988).
29. Krumlauf, R., *Cell*; 78, 191–201, (1994).
30. Boncinelli, E., et al., *Hum. Reproduc.*; 3, 880–886, (1988).
31. Lewis, E. B., *Nature*; 276, 565–570, (1978).
32. Kretzner, L., et al., *Nature*; 359, 426–429, (1992).
33. Blackwood, E., et al., *Science*; 251, 1211–1217, (1991).
34. Edlund, T., et al. *Science*; 230:912–916, (1985).
35. Clark, K., et al. *Nature*; 364:412–420 (1993).
36. Lai, E., et al. *PNAS*; 90:10421–10423 (1993).
37. Sharma, et al., *JBC*; 271:2294–2299 (1996).

What is claimed is:

1. A method for determining an ability of a test compound to stimulate pancreatic islet cells to induce STF-1 transcription, comprising the steps of:

providing a vector comprising in operable association an STF enhancer of SEQ ID NO: 1 or SEQ ID NO: 2 or fragments there of with STF enhancer activity, a promoter and a reporter gene, and wherein expression of the reporter gene confers a detectable signal to a pancreatic host cell;

introducing said vector into pancreatic islet host cells in vitro;

culturing said host cells in the presence of a test compound; and assaying for said compound to stimulate said host cells to produce said detectable signal, wherein the presence of said signal indicates that said test compound stimulates pancreatic islet cells to induce STF-1 transcription, and wherein the absence of said signal indicates that said test compound does not stimulate pancreatic cells to induce STF-1 transcription.

2. The method of claim 1, wherein said reporter gene is an enzyme.

3. The method of claim 2, wherein said enzyme is selected from the group of luciferase and β-galactosidase.

4. The method of claim 1, wherein said introduction is by transfection.

5. The method of claim 4, wherein said pancreatic islet cells are HIT cells.

6. The method of claim 1, wherein said cells are isolated from a transgenic non-human mammal whose genome comprises a DNA sequence comprising in operable association an STF enhancer of SEQ ID NO: 1 or SEQ ID NO: 2 or fragments there of with STF enhancer activity, a promoter and a reporter gene, such that expression of the reporter gene is induced by compounds that stimulate pancreatic cells to induce STF-1 transcription.

7. A method of marking insulin-producing pancreatic islet cells in vivo, comprising the steps of:

providing a vector comprising an STF-1 promoter operably linked to a reporter gene, wherein expression of the reporter gene confers a detectable signal to a pancreatic islet cell;

introducing said vector as a transgene to a non-human mammal embryo;

growing said embryo to a mammal with pancreatic islet cells; and assaying for said detectable signal to determine if any of said mammal's pancreatic islet cells express said reporter gene, wherein a presence of said detectable signal indicates the presence of insulin-producing pancreatic islet cells, and wherein the absence of said detectable signal indicates an absence of insulin-producing pancreatic islet cells.

8. The method of claim 7, wherein said reporter gene encodes a fluorescent protein.

9. The method of claim 8, wherein said method further includes a step of sorting insulin-producing pancreatic islet cells from non-insulin-producing pancreatic islet cells by fluorescence activated cell sorting (FACS).

* * * * *

UNITED STATES PATENT AND TRADEMARK OFFICE
CERTIFICATE OF CORRECTION

PATENT NO.   : 5,969,210
DATED        : October 19, 1999
INVENTOR(S)  : Seema Sharma and Marc R. Montminy It is certified that error appears in the above-identified patent and that said Letters Patent is hereby corrected as shown below:

Column 1,
Line 41, "i s" should read -- is --.

Column 5,
Line 40, "shows" should read -- show --.
Line 51, "shows" should read -- show --.
Lines 59-60, "(SEQ ID NO:1)" should read -- (SEQ ID NO:2) --.

Column 6,
Line 9, "see also FIG. 2B. bottom)" should read -- see also FIG. 2B) --.
Line 17, "shows" should read -- show --.
Line 39, "shows" should read -- show --.
Line 65, "illustrates" should read -- ilustrate --.

Column 7,
Line 15, "demonstrates" should read -- demonstrate --.
Line 35, delete the word "(Top)".
Line 49, "demonstrates" should read -- demonstrate --.

Column 8,
Line 24, "shows", should read -- show --.
Line 40, insert the word -- are -- between the words "bars" and "shown".

Column 9,
Line 28, insert a comma after the words "Ogawa et al.".

Column 10,
Line 38, "lement" should read -- element --.
Line 46, "b e" should read -- be --.
Line 54, "[B. D. Hames" should read -- (B. D. Hames --.
Line 55, "(1985)]" should read -- (1985)) -- and, "[B. D. Hames" should read -- (B. D. Hames --.
Line 56, "(1984)]" should read -- (1984)) -- and, "[R. I." should read -- (R. I. --.
Line 58, "[IRL Press, (1986)]" should read (IRL Press, (1986)) --.

Column 13,
Line 27, "i n" should read -- in --.
Line 50, "nstructed" should read -- constructed --.
Line 52, "thern" should read -- Southern --.

UNITED STATES PATENT AND TRADEMARK OFFICE
CERTIFICATE OF CORRECTION

PATENT NO. : 5,969,210
DATED : October 19, 1999
INVENTOR(S) : Seema Sharma and Marc R. Montminy It is certified that error appears in the above-identified patent and that said Letters Patent is hereby corrected as shown below:

Column 18,
Line 25, "7$a$" should read -- 7a --.
Line 28, "7$b$" should read -- 7b --.
Line 34, "7$c$" should read -- 7c --.
Line 45, "8$a$" should read -- 8a --.
Line 49 & 55, "8$a$" should read -- 8a --.
Lines 63 & 67, "8$b$" should read -- 8b --.

Column 19,
Line 5, "8$b$" should read -- 8b --.
Lines 17 & 19, "8$c$" should read -- 8c --.
Lines 32, 36 & 38, "8$d$" should read -- 8d --.
Line 48, "9$a$" should read -- 9a --.
Lines 57, 62, 64 & 67, "9$b$" should read -- 9b --.

Column 20,
Line 5, "9$c$" should read -- 9c --.
Line 11, "9$b$" should read -- 9b --.

Column 23, Claim 1,
Should read -- A method for determining an ability of a test compound to stimulate pancreatic islet cells to induce STF-1 transcription, comprising the steps of:
  providing a vector containing an STF-1 enhancer having a sequence selected from the group SEG ID No:1 or SEQ ID No:2 or fragments thereof, a promoter, and a reporter gene under the transcriptional control of both said STF-1 enhancer and said promoter, wherein said reporter gene is capapble of conferring a detectable signal to said host cell;
  transferring said vector into said host cell;
  culturing said host cell in the presence of a test compound to determine an ability of said test substance to stimlate said host cell to produce said signal; and
  assaying for said signal to determine said ability of said test compound to stimlate said host cell to produce said detectable signal, wherein a presence of said signal indicates that said test compound stimulates pancreatic islet cells to induce STF-1 transcription, and wherein an absence of said signal indicates that said test compound does not stimilate pancreatic islet cells to induce STF-1 transcription. --.

UNITED STATES PATENT AND TRADEMARK OFFICE
CERTIFICATE OF CORRECTION

PATENT NO.   : 5,969,210
DATED        : October 19, 1999
INVENTOR(S)  : Seema Sharma and Marc R. Montminy It is certified that error appears in the above-identified patent and that said Letters Patent is hereby corrected as shown below:

Column 25,
Line 14, "claim 4." should read -- claim 3. --.
Claim 6, should read -- The method of claim 1, wherein said transferring step is performed by microinjection introduction of a transgene into animals. --.

Column 26,
Line 17, "claim 7." should read -- claim 6. --.
Line 19, "claim 8." should read -- claim 7. --.

Signed and Sealed this

Ninth Day of October 2001

*Attest:*

NICHOLAS P. GODICI
*Attesting Officer*  Acting Director of the United States Patent and Trademark Office

UNITED STATES PATENT AND TRADEMARK OFFICE
CERTIFICATE OF CORRECTION

PATENT NO. : 5,969,210
DATED : October 19, 1999
INVENTOR(S) : Seema Sharma and Marc R. Montminy It is certified that error appears in the above-identified patent and that said Letters Patent is hereby corrected as shown below:

Column 1,
Line 41, "i s" should read -- is --.

Column 5,
Lines 40 and 51, "shows" should read -- show --.
Lines 59-60, "(SEQ ID NO:1)" should read -- (SEQ ID NO:2) --.

Column 6,
Line 9, "(see also FIG. 2B. bottom)" should read -- see also FIG. 2B) --.
Lines 17 and 39, "shows" should read -- show --.
Line 65, "illustrates" should read -- ilustrate --.

Column 7,
Lines 15 and 49, "demonstrates" should read -- demonstrate --.
Line 35, please delete the word "(Top)".

Column 8,
Line 24, "shows" should read -- show --.
Line 40, please insert the word -- are -- between the words "bars" and "shown".

Column 9,
Line 28, please insert a comma after the words "Ogawa et al.".

Column 10,
Line 38, "lement" should read -- element --.
Line 46, "b e" should read -- be --.
Lines 54 and 55, "[B. D. Hames" should read -- (B. D. Hames --.
Line 55, "(1985)]" should read -- (1985)) --.
Line 56, "(1984)]" should read -- (1984)) --.
Line 56, "[R. I." should read -- (R. I. --.
Line 58, "[IRL Press, (1986)]" should read -- (IRL Press, (1986)) --.

Column 13,
Line 27, "i n" should read -- in --.
Line 50, "nstructed" should read -- constructed --.
Line 52, "thern" should read -- Southern --.

UNITED STATES PATENT AND TRADEMARK OFFICE
CERTIFICATE OF CORRECTION

PATENT NO. : 5,969,210
DATED : October 19, 1999
INVENTOR(S) : Seema Sharma and Marc R. Montminy It is certified that error appears in the above-identified patent and that said Letters Patent is hereby corrected as shown below:

Column 18,
Line 25, "7$a$" should read -- 7a --.
Line 28, "7$b$" should read -- 7b --.
Line 34, "7$c$" should read -- 7c --.
Line 45, "8$a$" should read -- 8a --.
Lines 49 and 55, "8$a$" should read -- 8a --.
Lines 63 and 67, "8$b$" should read -- 8b --.

Column 19,
Line 5, "8$b$" should read -- 8b --.
Lines 17 and 19, "8$c$" should read -- 8c --.
Lines 32, 36 and 38, "8$d$" should read -- 8d --.
Line 48, "9$a$" should read -- 9a --.
Lines 57, 62, 64 and 67, "9$b$" should read -- 9b --.

Column 20,
Line 5, "9$c$" should read -- 9c --.
Line 11, "9$b$" should read -- 9b --.

Columns 23,
Claim 1, should read:
-- A method for determining an ability of a test compound to stimulate pancreatic islet cells to induce STF-1 transcription, comprising the steps of:
    providing a vector containing an STF-1 enhancer having a sequence selected from the group SEG ID No:1 or SEQ ID No:2 or fragments thereof, a promoter, and a reporter gene under the transcriptional control of both said STF-1 enhancer and said promoter, wherein said reporter gene is capable of conferring a detectable signal to said host cell;
    transferring said vector into said host cell;
    culturing said host cell in the presence of a test compound to determine an ability of said test substance to stimulate said host cell to produce said signal; and
    assaying for said signal to determine said ability of said test compound to stimulate said host cell to produce said detectable signal, wherein a presence of said signal indicates that said test compound stimulates pancreatic islet cells to induce STF-1 transcription, and wherein an absence of said signal indicates that said test compouind does not stimulate pancreatic islet cells to induce STF-1 transcription. --.

UNITED STATES PATENT AND TRADEMARK OFFICE
CERTIFICATE OF CORRECTION

PATENT NO. : 5,969,210
DATED : October 19, 1999
INVENTOR(S) : Seema Sharma and Marc R. Montminy It is certified that error appears in the above-identified patent and that said Letters Patent is hereby corrected as shown below:

Column 25,
Line 14, "claim 4." should read -- claim 3. --.
Lines 16-23, should read -- The method of claim 1, wherein said transferring step is performed by microinjection introduction of a transgene into animals. --.

Column 26,
Line 17, "claim 7." should read -- claim 6. --.
Line 19, "claim 8." should read -- claim 7. --.

Signed and Sealed this

Seventeenth Day of August, 2004

JON W. DUDAS
*Acting Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 403 bp
       (B) TYPE: nucleic acid
       (C) STRANDEDNESS: double
       (D) TOPOLOGY: linear (ii) MOLECULE TYPE:
       (A) DESCRIPTION: other nucleic acid (iii) HYPOTHETICAL: No (iv) ANTI-SENSE: No (vi) ORIGINAL SOURCE:
       (B) STRAIN:
       (C) INDIVIDUAL ISOLATE:
       (D) DEVELOPMENTAL STAGE:
       (F) TISSUE TYPE:
       (G) CELL TYPE:
       (H) CELL LINE:

(xi) SEQUENCE DESCRIPTION: SEQ ID NO:1:

```
TTAAGCTCTA ATGGAGCGGT TTTGTAACGG AGTAAAGGTT CTGATATTTT TGCGCTCCCC    60

GGTTTGGAGA GCTCCGCAGC AGGACAGGAG AGATCAGCCT GCTGAGAGAG AAAATTGAAA   120

CAAGTGCAGG TGTTCGCGGG CCTGGGCCTC CTTCTTAAGG CAGGGCCAGG CCAATGGTGG   180

CCCCAGGCTG AACCACGTGG GGTGCCTCAG AGCCTATGGC ACGGCGACCG GCTTCTCTGT   240

CTCTCGCCAG CCTGTGGTTC CCCGGGAGAG CAGTGGAGAA CTGTCAAAGC GATCTGGGGT   300

GGCGCTGAGA GTCCGTGAGC TGCCAGCGCC TTAAGGCCTG GCTTGTAGCT CCCTACCCCG   360

GGCTGCCGGC CCCGAAGTGC CGGCTGCCAC CATGAATAGT GAG                    403
```

(2) INFORMATION FOR SEQ ID NO:2:

(i) SEQUENCE CHARACTERISTICS:
       (A) LENGTH: 490 bp
       (B) TYPE: nucleic acid
       (C) STRANDEDNESS: double
       (D) TOPOLOGY: linear (ii) MOLECULE TYPE:
       (A) DESCRIPTION: other nucleic acid (iii) HYPOTHETICAL: No (iv) ANTI-SENSE: No (vi) ORIGINAL SOURCE:
       (B) STRAIN:
       (C) INDIVIDUAL ISOLATE:
       (D) DEVELOPMENTAL STAGE:
       (F) TISSUE TYPE:
       (G) CELL TYPE:
       (H) CELL LINE:

(xi) SEQUENCE DESCRIPTION: SEQ ID NO:2:

```
TCTAGAGAGT TCTCCTGTTC GCTAGATAAG AAAGCCTGTT CTGCCATCCC AGCAGGCATA    60

GGCTGTTTAA GTTACTAGAT AACAGAGTTG TTATTGATTC TATTATTATT ATTTTTTCTA   120

CTCTTCCTGA TTCCCTGAAG TCCAAGGGAA GTTTTGTCAA CTAGGAATGA TTTTTGTTTA   180
```

-continued

```
AAAAAAAAAA AAAAAGGCTC CTTGTTGTGT CTTAGCTGGT CAGTGACAGA TGGAGTCCTG    240

AGTTTCCTAG GAGCCCTTTA CTCAGGAGTG GGAGAACAGA AAGTAAATAA GCGCTCTTAG    300

TCATCTGCTT TCTCAGAGCA GCGTTGGGCC CCAGCACTTG GAAAGCGAAT GCTGGCTCCT    360

CCTGGACTCC CCCGTCAGCC TGATGTTGTT AACCCGTTTA ACATTCCCTT ATCACATGCT    420

CATTGTGGGC AGAATTAAGT GGAATTAGCT AACAAATTAT ATAAAATTCA TTTACCTTTC    480

AAGGAAGCTG                                                          490
```

(2) INFORMATION FOR SEQ ID NO:3:

(i) SEQUENCE CHARACTERISTICS:
        (A) LENGTH: 20bp
        (B) TYPE:nucleic acid
        (C) STRANDEDNESS: single
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:3:

```
TCAGTGACAG ATGGAGTCCT                                                20
```

(2) INFORMATION FOR SEQ ID NO:4:

(i) SEQUENCE CHARACTERISTICS:
        (A) LENGTH: 20 bp
        (B) TYPE: nucleic acid
        (C) STRANDEDNESS: single
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:4:

```
TCAGTGAAAG ACGGAGTCCT                                                20
```